United States Patent
Reda et al.

(10) Patent No.: US 9,589,361 B2
(45) Date of Patent: Mar. 7, 2017

(54) AUTOMATIC SEGMENTATION OF INTRA-COCHLEAR ANATOMY IN POST-IMPLANTATION CT OF UNILATERAL COCHLEAR IMPLANT RECIPIENTS

(71) Applicant: Vanderbilt University, Nashville, TN (US)

(72) Inventors: Fitsum A. Reda, Nashville, TN (US); Jack H. Noble, Nashville, TN (US); Benoit Dawant, Nashville, TN (US); Robert F. Labadie, Nashville, TN (US)

(73) Assignee: VANDERBILT UNIVERSITY, Nashville, TN (US)

( * ) Notice: Subject to any disclaimer, the term of this patent is extended or adjusted under 35 U.S.C. 154(b) by 10 days.

(21) Appl. No.: 14/766,402

(22) PCT Filed: Feb. 7, 2014

(86) PCT No.: PCT/US2014/015332
§ 371 (c)(1),
(2) Date: Aug. 6, 2015

(87) PCT Pub. No.: WO2014/124277
PCT Pub. Date: Aug. 14, 2014

(65) Prior Publication Data
US 2015/0379723 A1    Dec. 31, 2015

Related U.S. Application Data

(60) Provisional application No. 61/762,024, filed on Feb. 7, 2013, provisional application No. 61/837,028, filed on Jun. 19, 2013.

(51) Int. Cl.
*G06K 9/00* (2006.01)
*G06T 7/00* (2006.01)
(Continued)

(52) U.S. Cl.
CPC .............. *G06T 7/0095* (2013.01); *A61B 6/03* (2013.01); *A61B 6/50* (2013.01); *A61B 6/5211* (2013.01);
(Continued)

(58) Field of Classification Search
None
See application file for complete search history.

(56) References Cited

U.S. PATENT DOCUMENTS 6,754,376 B1   6/2004   Turek et al.
8,073,216 B2   12/2011  Dawant et al.
(Continued)

OTHER PUBLICATIONS

Reda et al ("Fully Automatic Surface-Based Pre to Intra-operative CT registration for Cochlear Implant", 2012).*

(Continued)

*Primary Examiner* — Avinash Yentrapati
(74) *Attorney, Agent, or Firm* — Locke Lord LLP; Tim Tingkang Xia, Esq.

(57) ABSTRACT

A method for automatic segmentation of intra-cochlear anatomy of a patient. The patient has an implanted ear and a normal contralateral ear. At least one computed tomography (CT) image is obtained to generate a first image corresponding to the normal contralateral ear and a second image corresponding to the implanted ear. Intra-cochlear surfaces of at least one first structure of interest (SOI) of the normal contralateral ear in the first image are segmented using at least one active shape model (ASM). Next, the segmented intra-cochlear surfaces in the first image is projected to the second image using a transformation function, thereby obtaining projected segmented intra-cochlear surfaces for the implanted ear in the second image.

44 Claims, 16 Drawing Sheets

(51) Int. Cl.

| | |
|---|---|
| *A61B 6/03* | (2006.01) |
| *A61B 6/00* | (2006.01) |
| *H04N 19/426* | (2014.01) |
| *G06T 3/00* | (2006.01) |
| *G06T 3/40* | (2006.01) |
| *A61N 1/05* | (2006.01) |

(52) U.S. Cl.
CPC .................. *G06T 3/00* (2013.01); *G06T 3/40* (2013.01); *G06T 7/0014* (2013.01); *G06T 7/0024* (2013.01); *G06T 7/0036* (2013.01); *G06T 7/0044* (2013.01); *G06T 7/0083* (2013.01); *G06T 7/0089* (2013.01); *G06T 7/0097* (2013.01); *H04N 19/428* (2014.11); *A61N 1/0541* (2013.01); *G06T 2207/10081* (2013.01); *G06T 2207/20016* (2013.01); *G06T 2207/20081* (2013.01); *G06T 2207/20124* (2013.01); *G06T 2207/20128* (2013.01); *G06T 2207/20132* (2013.01); *G06T 2207/30052* (2013.01)

(56) References Cited

U.S. PATENT DOCUMENTS

| | | | |
|---|---|---|---|
| 8,135,453 | B2 | 3/2012 | Slabaugh et al. |
| 2009/0060308 | A1* | 3/2009 | Dawant ................. G06T 7/0028 382/131 |

OTHER PUBLICATIONS

Nobel, Jack H. et al., "Automatic Identification of Cochlear Implant Electrode Arrays for Post-Operative Assessment", Proceedings of SPIE Int Soc Opt Eng., Mar. 11, 2011, pp. 1-10, vol. 7962.
Nobel, Jack H. et al., "Automatic Segmentation of Intracochlear Anatomy in Conventional CT", IEEE Transation on Biomedical Engineering, Sep. 2011, pp. 2625-2632, vol. 58, No. 9.
Korean Intellectual Property Office (ISR/KR), "International Search Report for PCT/CN2014/015332", Korea, May 26, 2014.
Arun, K.S., Huang, T.S., and Blostein, S.D. "Least-squares fitting of two 3-D point sets," IEEE Trans. Pattern Anal. Mach. Intell., vol. 9, No. 5, pp. 698-700, Sep. 1987.
Aschendorff, A., Kromeier, J., Klenzner, T., and Laszig, R., "Quality control after insertion of the nucleus contour and contour advance electrode in adults," Ear Hearing, vol. 28, pp. 75S-79S, Apr. 2007.
Besl, P.J., McKay, H.D., "A method for registration of 3-D shapes," Pattern Analysis and Machine Intelligence, IEEE Transactions on, 14(2):239-256, 1992.
Brejl, M., Sonka, M., 2000. Object localization and border detection criteria design in edge-based image segmentation: automated learning from examples. IEEE Transactions on Medical Imaging 19 (10), 973-985.
Chakraborty, A., Staib, L., Duncan, J.S.,. Deformable boundary finding in medical images by integrating gradient and region information. IEEE Transactions on Medical Imaging 15 (6), 859-870, 1996.
Cohen, L., Cohen, I., Finite-element methods for active contours models and balloons for 2-D and 3-D images. IEEE Transactions on Pattern Analysis and Machine Intelligence 15 (11), 1131-1147, 1993.
Cootes, T.F., Taylor, C.J., Cooper, D H., and Graham, J. "Active shape models—Their training and application," Comp. Vis. Image Understanding, vol. 61, No. 1, pp. 39-59, 1995.
Cootes, T.F., Taylor, C.J., Statistical models of appearance for medical image analysis and computer vision. In: Sonka, M., Hanson K.M. (Eds.), Proceedings of the SPIE Medical Imaging, vol. 4322, pp. 236-248, 2001.
Fitsum A. Reda, Jack H. Noble, Robert F. Labadie, and Benoit M. Dawant, "An artifact-robust technique for automatic segmentation of the labyrinth in post-cochlear implantation CT", Proc. SPIE 9034(9034-103), Medical Imaging 2014.
Heimann, T., Wolf, I., Meinzer, H.-P., Active shape models for a fully automated 3D segmentation of the liver—an evaluation on clinical data. In: Larsen, R., Nielsen, M., Sporring, J. (Eds), Proceeding of MICCAI, LNCS, vol. 4191. Springer, pp. 41-48, 2006.
Heimann, T., and Meinzer, H-P., "Statistical shape models for 3D medical image segmentation: A review", Medical Image Analysis, vol. 13(4), pp. 543-563, Aug. 2009.
Jack H. Noble, Theodore A. Schuman, Charles G. Wright, Robert F. Labadie, Benoit M. Dawant, "Automatic dentification of cochlear implant electrode arrays for post-operative assessment", Proc. SPIE 7962(796217), Medical Imaging 2011b.
Jeffery, N. and Spoor, F., Prenatal growth and development of the modem human labyrinth. Journal of Anatomy, 204: 71-92, 2004.
Kass, M., Witkin, A., Terzopoulos, D., Snakes: active contour models. International Journal of Computer Vision 1 (4), 321-331, 1988.
Liu, Y., Collins, R. T., and Rothfus, W. E., "Robust midsagittal plane extraction from normal and pathological 3D neuroradiology images," IEEE Trans. on Medical Imaging, vol. 20, No. 3, pp. 175-192, Mar. 2001.
Maes, F., Collignon, A., Vandermeulen, D., Mrchal, G., and Suetens, P. "Multimodality image registration by maximization of mutual information," IEEE Trans. Med. Imag., vol. 16, No. 2, pp. 187-198, Apr. 1997.
Mitchell, S.C., Lelieveldt, B.P.F., van der Geest, R.J., Bosch, H.G., Reiber, J.H.C., Sonka, M.,. Multistage hybrid active appearance model matching: segmentation of left and right ventricles in cardiac MR images. IEEE Transactions on Medical Imaging 20(5), 415-423, 2001.
Noble, J.H., Labadie, R.F., Majdani, O., Dawant, B.M., "Automatic Segmentation of Intracochlear Anatomy in Conventional CT," Biomedical Engineering, IEEE Transactions on, 58(9):2625-2632, Sep. 2011a.
Noble, J.H., Gifford, R.H., Labadie, R.F., Dawant, B.M., "Statistical Shape Model Segmentation and Frequency Mapping of Cochlear Implant Stimulation Targets in CT," MICCAI 2012, 421-428, 2012.
Noble, J.H., Labadie, R.F., Gifford, R.H., Dawant, B.M., "Image-guidance enables new methods for customizing cochlear implant stimulation strategies," Neural Systems and Rehabilitation Engineering, IEEE Transactions on 21 (5):820-829, Sep. 2013.
Press, W.H., Flannery, B.P., Teukolsky, S.A., and Vetterling, W.T. Numerical Recipes in C, 2nd ed. (Cambridge University press, Cambridge, 1992), pp. 412-419.
Prima, S.; Ourselin, S.; Ayache N., "Computation of the mid-sagittal plane in 3-D brain images," Medical Imaging, IEEE Transactions on, vol. 21, No. 2, pp. 122,148, Feb. 2002.
Rohde, G.K, Aldroubi, A., and Dawant, B.M. "The adaptive bases algorithm for intensity-based nonrigid image registration," IEEE Trans. Med. Imaging, 22(11), 1470-1479 (2003).
Ruppert, G.C.S.; Teverovisky, L.; Chen-Ping Yu; Falaco, A.X.; Yanxi Liu, "A new symmetry based method for mid-sagittal plane extraction in neuroimages", Biomedical Imaging: From Nano to Macro, 2011 IEEE International Symposium on, On pages(s): 285-288.
Sakalli, M., Lam, K.-M., Yan, H., A faster converging snake algorithm to locate object boundaries. IEEE Transactions on Image Processing 15 (5), 1182-1191, 2006.
Schuman T.A., Noble J.H., Wright C.G., Wanna G.B., Dawant B.M., Labadie, R.F. "Anatomic Verification of a Novel, Non-rigid Registration Method for Precise Intrascalar Localization of Cochlear Implant Electrodes in Adult Human Temporal Bones Using Clinically-available Computerized Tomography," The Laryngoscope, 120 (11): 2277-2283, 2010.
Smith, S. M. and Jenkinson, M., "Accurate robust symmetry estimation," in Proc MICCAI '99, London, UK, 1999, pp. 308-317, Springer-Verlag.
Sonka, M. and Fitzpatrick, J.M. "Medical Image Processing and Analysis," Handbook of Medical Imaging, vol. 2, chapter 8:369-70, 2000.

(56) References Cited

OTHER PUBLICATIONS

Staib, L.H., Duncan, J.S.,. Boundary finding with parametically deformable models. IEEE Transactions on Pattern Analysis and Machine Intelligence 14 (11), 1061-1075, 1992.

Studholme, C., Hill, D.L.G., and Hawkes, D.J. "An overlap invariant entropy measure of 3D medical image alignment," Pattern Recognition, 32(1):71-86, 1999.

Tobon-Gomez, C., Butakoff, C., Aguade, S., Sukno, F., Moragas, G., Frangi, A.F., Automatic construction of 3D-ASM intensity models by simulating image acquisition: application to myocardial gated SPECT studies. IEEE Transactions on Medical Imaging 27 (11), 1655-1667, 2008.

Tuzikov, A.V., Colliot, O., Bloch, I., "Evaluation of the symmetry plane in 3D MR brain images," Pattern Recognition Letters, vol. 24, No. 14, pp. 2219-2233, Oct. 2003.

Wanna, G.B., Noble, J.H., McRackan, T.R., Dawant, B.M., Dietrich, M.S., Watkins, L.D., Rivas, A., Schuman, T.A., Labadie, R.F., "Assessment of electrode positions and audiological outcomes in bilateral cochlear implant patients," Otology & Neurotology, 32(3):428-432, 2011.

Wells III, W.M., Viola, P., Atsumi, H., Nakajima, S. and Kikinis, R. "Multi-modal volume registration by maximization of mutual information," Med. Image Anal., vol. 1, No. 1, pp. 35-51, Mar. 1996.

Wilson B.S., Finley C.C., Lawson, D.T., Wolford, R.D., Eddington, D.K., Rabinowitz, W.M., "Better speech recognition with cochlear implants," Nature 352, 236-238, 1991.

Wilson B.S., Dorman M.F., "Cochlear implants: Current designs and future possibilities," J. Rehab. Res. Dev. 45(5): 695-730, 2008.

Wu, Z., "Multivariate compactly supported positive definite radial basis functions," Adv. Comput. Math., vol. 4, pp. 283-292, 1995.

Poznyakovskiy, Anton A. et al., "The creation of geometric three-dimensional models of the inner ear based on micro computer tomography data", Hearing Research, 2008, pp. 95-104, vol. 243.

European Patent Office, "Supplementary European Search Report for EP Appln No. 14 749 479.3", Munich, Germany, Jul. 8, 2016.

\* cited by examiner

AUTOMATIC SEGMENTATION OF INTRA-COCHLEAR ANATOMY IN POST-IMPLANTATION CT OF UNILATERAL COCHLEAR IMPLANT RECIPIENTS

CROSS-REFERENCE TO RELATED PATENT APPLICATIONS

This application claims priority to and the benefit of, pursuant to 35 U.S.C. §119(e), U.S. Provisional Patent Application Ser. No. 61/762,024, filed Feb. 7, 2013, and U.S. Provisional Patent Application Ser. No. 61/837,028, filed Apr. 19, 2013. The disclosures of the above applications are incorporated herein in their entireties by reference.

Some references, which may include patents, patent applications and various publications, are cited and discussed in the description of this disclosure. The citation and/or discussion of such references is provided merely to clarify the description of the present disclosure and is not an admission that any such reference is "prior art" to the disclosure described herein. All references cited and discussed in this specification are incorporated herein by reference in their entireties and to the same extent as if each reference was individually incorporated by reference.

STATEMENT AS TO RIGHTS UNDER FEDERALLY-SPONSORED RESEARCH

This invention was made with government support under grant numbers R01DC008408, R21DC012620 and R01DC010184 awarded by the National Institute on Deafness and Other Communication Disorders. The government has certain rights in the invention.

FIELD OF THE INVENTION

The invention relates generally to methods and systems for automatic segmentation of intra-cochlear anatomy in post-implantation CT.

BACKGROUND OF THE INVENTION

A cochlear implant (CI) is a neural prosthetic device that restores hearing by directly stimulating the auditory nerve using an electrode array that is surgically implanted in the cochlea (U.S. Food and Drug Administration, 1995). An external sound processor, typically worn behind the ear, processes sounds detected by a microphone into signals sent to the implanted electrodes. The CI sound processor is programmed after implantation by an audiologist. Based on patient response, the audiologist determines stimulation levels for each electrode and selects a frequency allocation table to define which electrodes should be activated when specific sound frequencies are detected (Wilson et al., 1991). The number of electrodes in a CI electrode array ranges from 12 to 22, depending on the manufacturer.

CI electrode arrays are designed such that when optimally placed in the scala tympani cavity of the cochlea, each electrode stimulates regions of the auditory nerve corresponding to a pre-defined frequency bandwidth (Wilson et al., 2008). However, because the surgeon threads the electrode array blind to internal cavities of the cochlea during the surgery, the final position of the electrode array relative to intra-cochlear anatomy is generally unknown. Research has shown that in 73% of CI surgeries the electrode array is placed fully within the scala tympani, while in the other 27% of CI surgeries, the electrode array is fully within a neighboring cavity or is initially inserted into the scala tympani but crosses into a neighboring cavity (Aschendorff et al., 2007). So far, the only option when programming the CI has been to assume the array is optimally placed in the cochlea and to use a default frequency allocation table. However, interpretation error in the locations of the CI device often occurs, resulting in poor programming of the CI and un-optimized sound effect.

Therefore, a heretofore unaddressed need exists in the art to address the aforementioned deficiencies and inadequacies.

SUMMARY OF THE INVENTION

In one aspect, the present invention is directed to a method for automatic segmentation of intra-cochlear anatomy of a patient having an implanted ear and a normal contralateral ear. In one embodiment, the method includes:

obtaining at least one computed tomography (CT) image to generate a first image corresponding to the normal contralateral ear and a second image corresponding to the implanted ear;

segmenting intra-cochlear surfaces of at least one first structure of interest (SOI) of the normal contralateral ear in the first image using at least one active shape model (ASM); and projecting the segmented intra-cochlear surfaces in the first image to the second image using a transformation function, thereby obtaining projected segmented intra-cochlear surfaces for the implanted ear in the second image.

In one embodiment, the transformation function is determined by rigidly registering a mirrored labyrinth surface of the first image to the second image.

In one embodiment, the step of segmenting intra-cochlear surfaces of the normal contralateral ear in the first image further includes: segmenting a surface of a labyrinth of the normal contralateral ear in the first image using the at least one ASM.

In one embodiment, the labyrinth is a structure that externally bounds the intra-cochlear anatomy and includes three semi-circular canals.

In one embodiment, the at least one first SOI is scala tympani (ST), scala vestibuli (SV), or spiral ganglion (SG).

In one embodiment, the at least one ASM is a labyrinth ASM, a scala tympani (ST) ASM, a scala vestibuli (SV) ASM, a spiral ganglion (SG) ASM, or a combination thereof.

In one embodiment, the labyrinth ASM is created using a plurality of pre-implantation images. One of the plurality of pre-implantation images is chosen as a reference volume and the remaining pre-implantation images are used as training volumes. The labyrinth ASM is created by:

manually segmenting a reference labyrinth in the reference volume;

registering training volumes to the reference volume and determining a registration transformation function for registering the training volumes to the reference volume;

pre-segmenting automatically a training labyrinth in each of the training volumes by projecting a reference surface of the reference volume onto the training volumes with the registration transformation function to generate labyrinth surfaces in the training volumes;

manually adjusting the generated labyrinth surfaces;

registering the adjusted labyrinth surfaces to the reference surface; and building the labyrinth ASM using an eigenanalysis method.

In one embodiment, in the step of the registering the training volumes to the reference volume, the registration transformation function is determined by:

downsampling a floating image and a fixed image, wherein the floating image is an image to be segmented, and the fixed image is an atlas image;

affinely registering the floating image to the fixed image;

cropping an ear region from the affinely registered floating image;

affinely registering the ear region of the floating image to an ear region of the fixed image at full image resolution; and non-rigidly registering the ear region of the floating image to the ear region of the fixed image to obtain the registration transformation function.

In one embodiment, the floating image and the fixed image are downsampled by a factor of 1-40 in each dimension. In one embodiment, the floating image and the fixed image are downsampled by a factor of 2-10 in each dimension. In one embodiment, the floating image and the fixed image are downsampled by a factor of 4 in each dimension.

In one embodiment, the step of segmenting intra-cochlear surfaces of the normal contralateral ear in the first image includes:

automatically initializing a shape in the first image, including:

registering the reference volume of the ASM to a target volume, wherein the target volume is the first image; and projecting points of a mean shape of the ASM onto the target volume to generate a projected ASM surface and fitting the ASM to projected points on the projected ASM surface;

adjusting the projected points, including:

obtaining a candidate point set comprising a plurality of candidate points, wherein each candidate point is located along a normal direction of a corresponding projected point on the projected ASM surface; and fitting the projected ASM surface to the candidate point set; and iterating the step of adjusting the projected points until convergence.

In one embodiment, the step of registering the reference volume of the ASM to a target volume includes:

downsampling the first image and the ASM to generate a downsampled first image and a downsampled ASM;

affinely registering the downsampled first image to the downsampled ASM;

cropping an ear region from the affinely registered first image;

affinely registering the ear region of the first image to an ear region of the ASM at full image resolution; and non-rigidly registering the ear region of the first image to the ear region of the ASM.

In one embodiment, the step of projecting the segmented intra-cochlear surfaces in the first image to the second image includes:

(1) automatically initializing a position of a projected labyrinth surface in the second image, including:

rigidly registering a mirrored image of the first image to the second image; and projecting a surface of a labyrinth of the normal contralateral ear in the first image to the second image to obtain an initial point set of the projected labyrinth surface, wherein the initial point set comprises a plurality of initial points;

(2) adjusting the position of the projected labyrinth surface, including:

obtaining a candidate point set comprising a plurality of candidate points, wherein each candidate point is located along a normal direction of a corresponding initial point on the projected labyrinth surface;

assigning a weight to each candidate point of the candidate point set; and rigidly registering the initial point set to the candidate point set; and (3) iterating the step (2) until convergence.

In one embodiment, the step of projecting the surface of the labyrinth of the normal contralateral ear in the first image to the second image is performed using the transformation function, and the transformation function is determined by:

initializing a mirroring transformation, comprising:

rigidly registering a target image to an atlas image having a pre-defined mid-sagittal plane, wherein the target image is the second image and the atlas image is the first image;

mirroring the target image along the pre-defined mid-sagittal plane to form a mirrored image; and projecting the mirrored image back onto the original target image;

refining the mirroring transformation; and projecting the surface of the labyrinth of the normal contralateral ear in the first image to the second image.

In another aspect, the present invention is directed to a method for automatic segmentation of intra-cochlear anatomy of a patient having an implanted ear and a normal contralateral ear. The method includes:

obtaining at least one computed tomography (CT) image to generate a first image corresponding to the normal contralateral ear and a second image corresponding to the implanted ear;

segmenting intra-cochlear surfaces of the normal contralateral ear in the first image; and projecting the segmented intra-cochlear surfaces in the first image to the second image using a transformation function, thereby obtaining projected segmented intra-cochlear surfaces for the implanted ear in the second image.

In one embodiment, the transformation function is determined by rigidly registering a mirrored labyrinth surface of the first image to the second image.

In one embodiment, the step of segmenting intra-cochlear surfaces of the normal contralateral ear in the first image includes segmenting at least one first structure of interest (SOI) in the first image using at least one active shape model (ASM).

In one embodiment, the step of segmenting intra-cochlear surfaces of the normal contralateral ear in the first image further includes segmenting a surface of a labyrinth of the normal contralateral ear in the first image using the at least one ASM.

In one embodiment, the labyrinth is a structure that externally bounds the intra-cochlear anatomy and includes three semi-circular canals.

In one embodiment, the at least one first SOI is scala tympani (ST), scala vestibuli (SV), or spiral ganglion (SG).

In one embodiment, the at least one ASM is a labyrinth ASM, a scala tympani (ST) ASM, a scala vestibuli (SV) ASM, a spiral ganglion (SG) ASM, or a combination thereof.

In one embodiment, the labyrinth ASM is created using a plurality of pre-implantation images. One of the plurality of pre-implantation images is chosen as a reference volume and the remaining pre-implantation images are used as training volumes. The labyrinth ASM is created by:

manually segmenting a reference labyrinth in the reference volume;

registering training volumes to the reference volume and determining a registration transformation function for registering the training volumes to the reference volume;

pre-segmenting automatically a training labyrinth in each of the training volumes by projecting a reference surface of the reference volume onto the training volumes with the registration transformation function to generate labyrinth surfaces in the training volumes;

manually adjusting the generated labyrinth surfaces;

registering the adjusted labyrinth surfaces to the reference surface; and building the labyrinth ASM using an eigenanalysis method.

In one embodiment, in the step of the registering the training volumes to the reference volume, the registration transformation function is determined by:

downsampling a floating image and a fixed image, wherein the floating image is an image to be segmented, and the fixed image is an atlas image;

affinely registering the floating image to the fixed image;

cropping an ear region from the affinely registered floating image;

affinely registering the ear region of the floating image to an ear region of the fixed image at full image resolution; and non-rigidly registering the ear region of the floating image to the ear region of the fixed image to obtain the registration transformation function.

In one embodiment, the floating image and the fixed image are downsampled by a factor of 1-40 in each dimension. In one embodiment, the floating image and the fixed image are downsampled by a factor of 2-10 in each dimension. In one embodiment, the floating image and the fixed image are downsampled by a factor of 4 in each dimension.

In one embodiment, the step of segmenting intra-cochlear surfaces of the normal contralateral ear in the first image includes:

automatically initializing a shape in the first image, including:
  registering the reference volume of the ASM to a target volume, wherein the target volume is the first image; and
  projecting points of a mean shape of the ASM onto the target volume to generate a projected ASM surface and fitting the ASM to projected points on the projected ASM surface;
adjusting the projected points, including:
obtaining a candidate point set comprising a plurality of candidate points, wherein each candidate point is located along a normal direction of a corresponding projected point on the projected ASM surface; and
fitting the projected ASM surface to the candidate point set; and iterating the step of adjusting the projected points until convergence.

In one embodiment, the step of registering the reference volume of the ASM to a target volume includes:

downsampling the first image and the ASM to generate a downsampled first image and a downsampled ASM;

affinely registering the downsampled first image to the downsampled ASM;

cropping an ear region from the affinely registered first image;

affinely registering the ear region of the first image to an ear region of the ASM at full image resolution; and non-rigidly registering the ear region of the first image to the ear region of the ASM.

In one embodiment, the step of projecting the segmented intra-cochlear surfaces in the first image to the second image includes:

(1) automatically initializing a position of a projected labyrinth surface in the second image, including:
  rigidly registering a mirrored image of the first image to the second image; and
  projecting a surface of a labyrinth of the normal contralateral ear in the first image to the second image to obtain an initial point set of the projected labyrinth surface, wherein the initial point set comprises a plurality of initial points;

(2) adjusting the position of the projected labyrinth surface, including:
  obtaining a candidate point set comprising a plurality of candidate points, wherein each candidate point is located along a normal direction of a corresponding initial point on the projected labyrinth surface;
  assigning a weight to each candidate point of the candidate point set; and
  rigidly registering the initial point set to the candidate point set; and (3) iterating the step (2) until convergence.

In one embodiment, the step of projecting the surface of the labyrinth of the normal contralateral ear in the first image to the second image is performed using the transformation function, and the transformation function is determined by:

initializing a mirroring transformation, comprising:
  rigidly registering a target image to an atlas image having a pre-defined mid-sagittal plane, wherein the target image is the second image and the atlas image is the first image;
  mirroring the target image along the pre-defined mid-sagittal plane to form a mirrored image; and
  projecting the mirrored image back onto the original target image;
refining the mirroring transformation; and
projecting the surface of the labyrinth of the normal contralateral ear in the first image to the second image.

In a further aspect, the present invention is directed to a non-transitory computer-readable medium storing instructions which, when executed by a processor, cause a computer to perform the methods as described above.

These and other aspects of the present invention will become apparent from the following description of the preferred embodiments, taken in conjunction with the following drawings, although variations and modifications therein may be affected without departing from the spirit and scope of the novel concepts of the disclosure.

BRIEF DESCRIPTION OF THE DRAWINGS

The accompanying drawings illustrate one or more embodiments of the disclosure and, together with the written description, serve to explain the principles of the disclosure. The same reference numbers may be used throughout the drawings to refer to the same or like elements in the embodiments.

FIG. 15A shows mean error for the ST (left), SV (middle), and SG (right) on all testing image pairs, and FIG. 15B shows maximum error for the ST (left), SV (middle), and SG (right) on all testing image pairs.

DETAILED DESCRIPTION OF THE INVENTION

Figure 1:
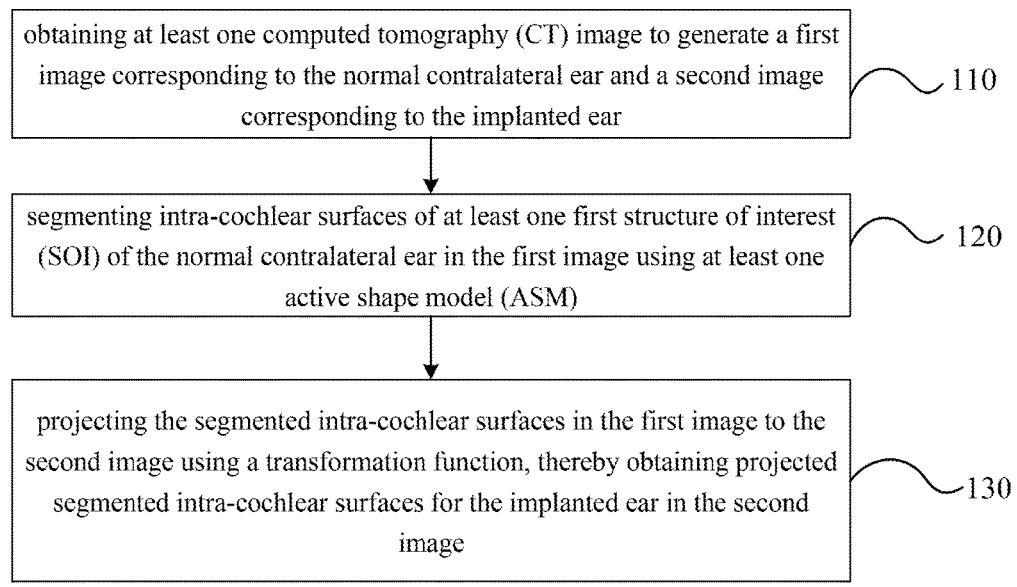
FIG. 1 shows a flowchart of automatic segmentation of intra-cochlear anatomy in a post-implantation computed tomography (CT) image according to one embodiment of the present invention.

The invention will now be described more fully hereinafter with reference to the accompanying drawings, in which exemplary embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like reference numerals refer to like elements throughout.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the invention.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another element as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The exemplary term "lower", can therefore, encompasses both an orientation of "lower" and "upper," depending of the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

As used herein, "around", "about", "substantially" or "approximately" shall generally mean within 20 percent, preferably within 10 percent, and more preferably within 5 percent of a given value or range. Numerical quantities given herein are approximate, meaning that the term "around", "about" "substantially" or "approximately" can be inferred if not expressly stated.

The description will be made as to the embodiments of the invention in conjunction with the accompanying drawings in FIGS. 1-17. In accordance with the purposes of this invention, as embodied and broadly described herein, this invention, in one aspect, relates to a drug delivery device and applications of the same in an image-guided surgery.

The following is an example according to certain embodiment of the present invention, to validate the method and to show the application of the present invention.

1. Introduction

Figures 2A, 2B:
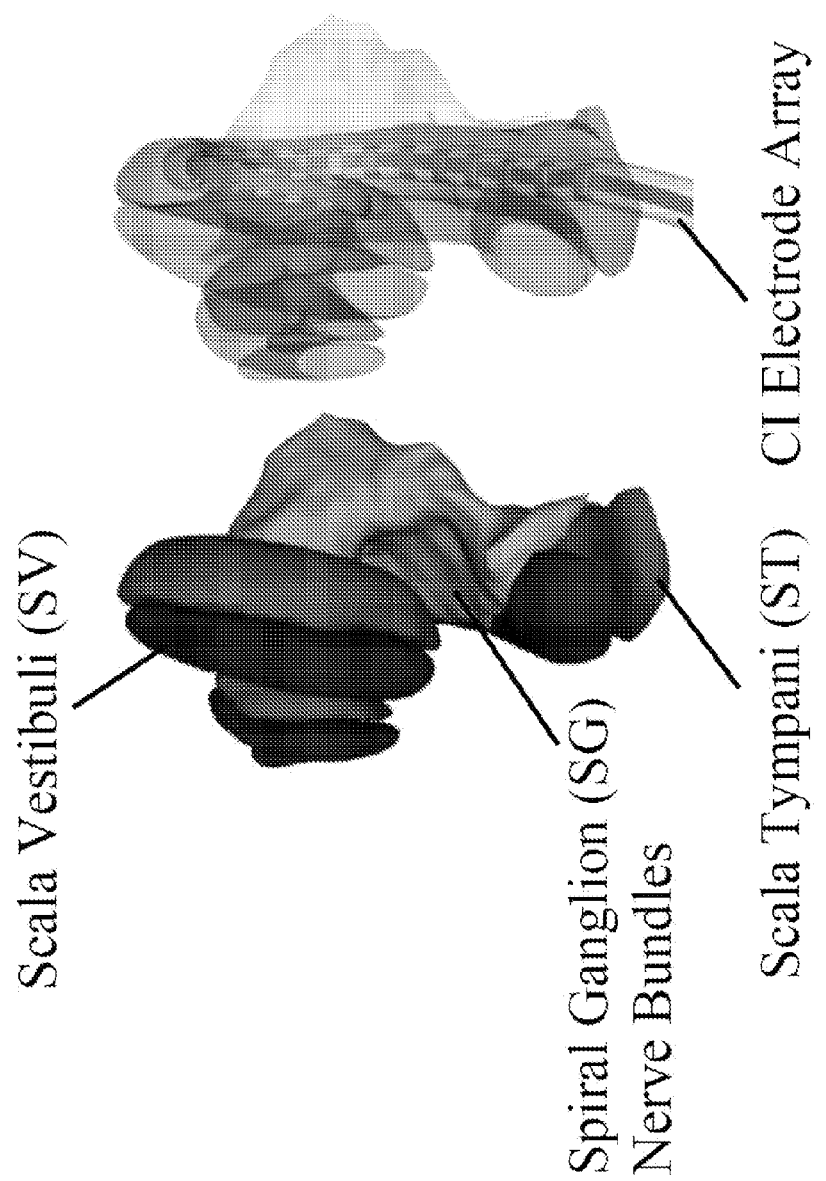
FIG. 2A shows the intra-cochlear structures-of-interest (SOIs), including scala tympani (ST), scala vestibuli (SV), and spiral ganglion (SG), according to one embodiment of the present invention.
FIG. 2B shows a surface model of a CI electrode array inserted into ST according to one embodiment of the present invention.

In one aspect, the present invention is directed to Image-Guided CI Programming (IGCIP) strategies. The IGCIP strategies rely on patient-specific knowledge of the position of the electrodes relative to intra-cochlear anatomy. It is shown that IGCIP strategies can drastically improve hearing outcomes (Noble et al., 2013). In one embodiment, IGCIP strategies are enabled by a number of algorithms that permit determining the spatial relationship between intra-cochlear anatomy and the CI electrodes using a pre-implantation and a post-implantation CT (Noble et al., 2011a, 2011b, 2012; Schuman et al., 2010; Wanna et al., 2011). The intra-cochlear Structures-Of-Interest (SOIs) are the scala tympani (ST), scala vestibuli (SV), and the spiral ganglion (SG), which is the ganglion of auditory nerve bundles. 3D renderings of these structures as well as the implant are shown in FIGS. 2A and 2B. Examples of pre- and post-implantation CTs with overlaid structure contours are shown in FIGS. 3A-4B. In one embodiment, the approach for determining electrode array position relative to the SOIs involves several steps. First, segmenting the SOIs in the pre-implantation CT. Next, identifying the electrode array in the post-implantation CT. Finally, rigidly registering the two CT images to determine the position of the electrodes relative to intra-cochlear anatomy.

However, this approach cannot be used for many CI recipients because it requires a pre-implantation CT, which is not always acquired prior to implantation. Thus far, the pre-implantation rather than the post-implantation CT has been used to identify the SOIs because the cochlea is obscured by image artifacts introduced by the metallic electrode array in the post-implantation CT (FIG. 3B and FIG. 4B).

Accordingly, in another aspect, the present invention is directed to methods to extend the IGCIP strategies to the population of unilateral CI recipients for whom a CT was not acquired pre-operatively, thereby increasing the portion of the population of existing CI recipients who can benefit from IGCIP strategies. In one embodiment, the methods permit automatic segmentation of the SOIs in the post-implantation CT despite the significant artifacts induced by the CI electrodes in those images.

FIG. 1 shows a flowchart of a method for automatic segmentation of intra-cochlear anatomy of a patient according to one embodiment of the present invention. The patient has an implanted ear and a normal contralateral ear. The method illustrated in FIG. 1 is provided as one embodiment and is not intended to limit the scope of the invention.

In step 110, at least one computed tomography (CT) image is obtained to generate a first image corresponding to the normal contralateral ear and a second image corresponding to the implanted ear. In one embodiment, one CT image is obtained. Alternatively, a series of CT images of a patient may be obtained. In one embodiment, some or all the CT images are post-implantation CT images. In one embodiment, both ears of the patient are in the field of view in the post-implantation CT images. In another embodiment, only one ear of the patient is in the field of view of one CT image.

In step 120, intra-cochlear surfaces of the normal contralateral ear in the first image are segmented using at least one active shape model (ASM). The intra-cochlear surfaces of the normal contralateral ear can include surfaces of structure of interests (SOIs). In one embodiment, the SOIs may include ST, SV and SG.

In step 130, the segmented intra-cochlear surfaces in the first image is projected to the second image using a transformation function, thereby obtaining projected segmented intra-cochlear surfaces for the implanted ear in the second image. In one embodiment, the transformation function is determined by rigidly registering a mirrored labyrinth surface of the first image to the second image.

In one embodiment, the transformation function is calculated substantially based on the labyrinth structure of the normal ear and the projected labyrinth surface in the image of the implanted ear. Based on this extracted information from the labyrinth structures of the normal ear and the implanted ear, the SOIs in the image of the normal ear are projected to the image of the implanted ear, so as to determine the positions of the projected SOIs in the image of the implanted ear.

FIG. 2A shows the intra-cochlear structures-of-interest (SOIs), including scala tympani (ST), scala vestibuli (SV), and spiral ganglion (SG), according to one embodiment of the present invention, and FIG. 2B shows a surface model of a CI electrode array inserted into ST according to one embodiment of the present invention. As shown in FIG. 2A and FIG. 2B, surface of ST is colored red, surface of SV is colored blue, and surface of SG is colored green.

Figure 3A:
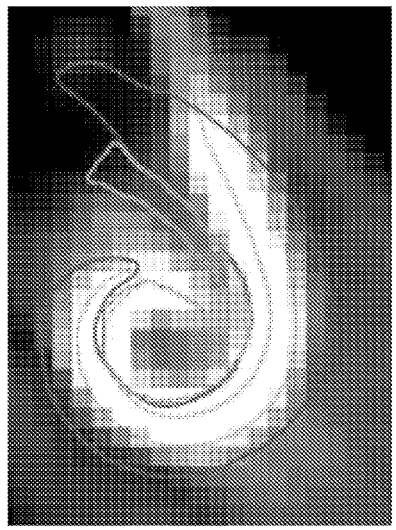
FIG. 3A and FIG. 3B show contours of ST (red), SG (green) and the electrodes (purple) in the coronal view of a pre-implantation CT and a corresponding post-implantation CT, respectively, according to one embodiment of the present invention.
Figure 3B:
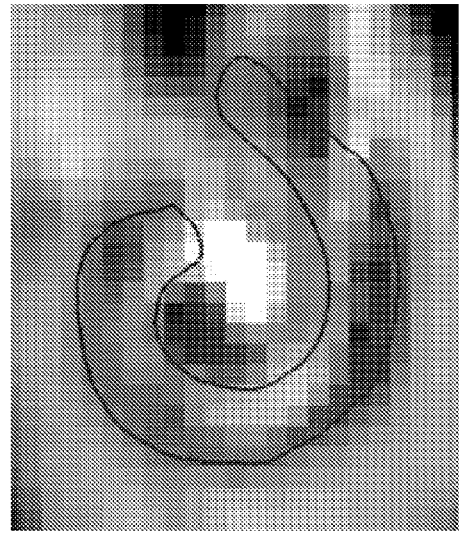

FIGS. 3A and 3B show contours of ST (red), SG (green) and the electrodes (purple) in the coronal view of a pre-implantation CT and a corresponding post-implantation CT, respectively, according to one embodiment of the present invention.

Figure 4A:
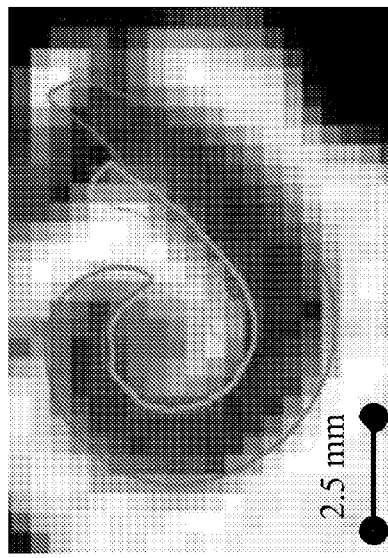
FIG. 4A and FIG. 4B show contours of the SV (blue) in the coronal view of a pre-implantation CT and a corresponding post-implantation CT, respectively, according to one embodiment of the present invention.
Figure 4B:
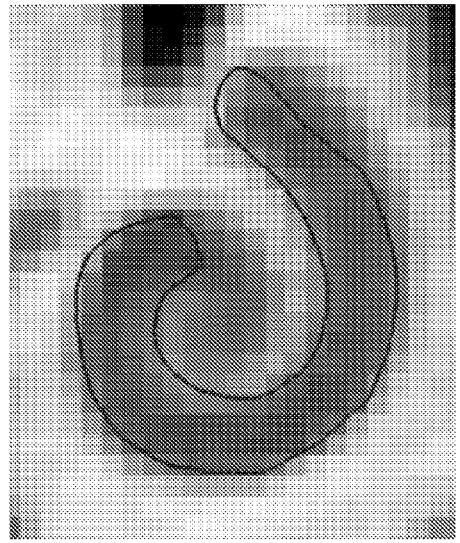

FIGS. 4A and 4B show contours of the SV (blue) in the coronal view of a pre-implantation CT and a corresponding post-implantation CT, respectively, according to one embodiment of the present invention. As shown in FIG. 4A and FIG. 4B, the bright structure in the post-implantation CTs is the artifact cause by the CI electrode array.

2. Methods

Figures 5A, 5B, 5C:
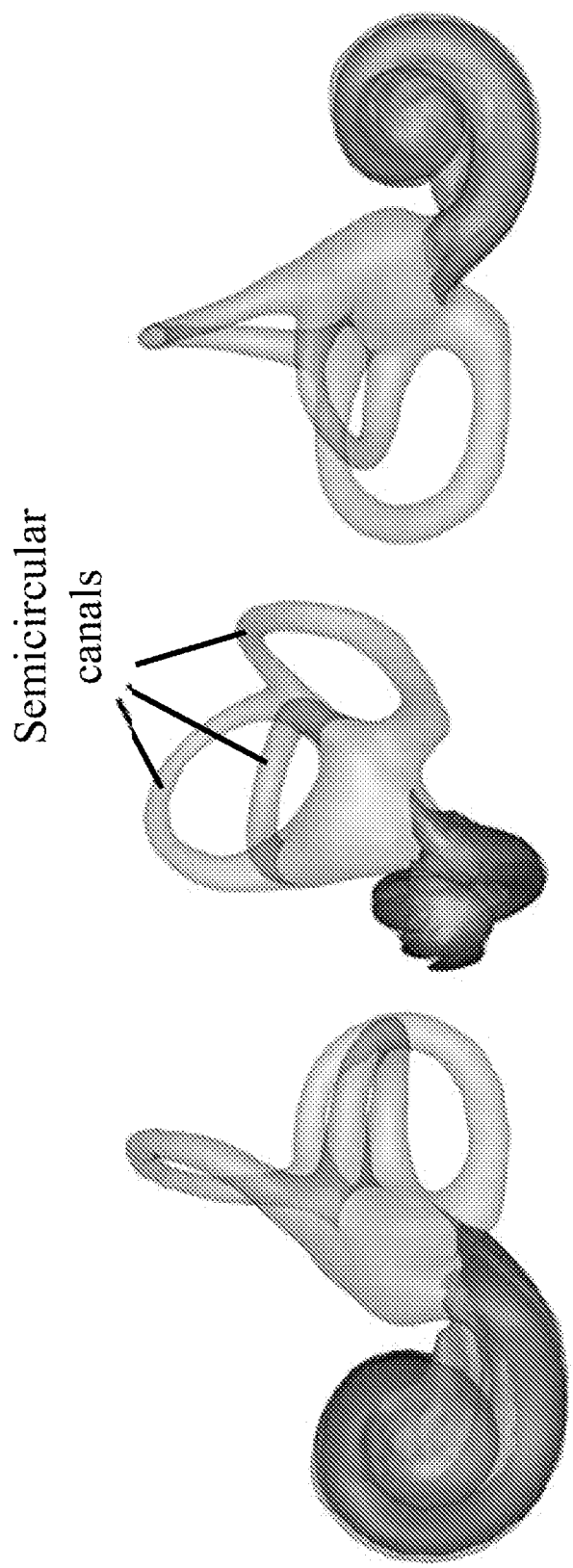
FIGS. 5A-5C show three different views of the labyrinth, which is used as a landmark structure, externally bounds the intra-cochlear anatomy and includes the three semicircular canals according to one embodiment of the present invention.

In one embodiment, the method for segmenting the intra-cochlear anatomy of unilateral CI recipients takes advantage of the intra-subject inter-ear symmetry the inventors have observed. A post-implantation CT is acquired in which both ears are in the field of view. Then the intra-cochlear anatomy of the implanted ear is segmented using information extracted from the normal contralateral ear. Specifically, segmentation is performed in the normal contralateral ear to the ST, SV, SG, which are the SOIs, and the labyrinth. The labyrinth, which is used as a landmark structure, externally bounds the intra-cochlear anatomy and includes the three semicircular canals, as shown in FIGS. 5A-5C. Next, segmentation is performed to the SOIs in the implanted ear by projecting the SOI surfaces from the normal ear to the implanted ear. The transformation used is the one that rigidly registers the mirrored labyrinth surface from the normal ear to the labyrinth in the implanted ear. The labyrinth provides adequate landmarks for this registration because a portion of the labyrinth lies far enough from the implant that its image features are not drastically affected by the implanted electrode array and, as shown below, the position of the labyrinth well predicts the position of the SOIs.

In one embodiment, the methods are detailed in the following subsections. In Section 2.1, details about the datasets are presented. In Section 2.2, the registration processes used at several steps throughout certain embodiments of the present invention are detailed. In Section 2.3, the study performed to establish inter-ear symmetry of cochlear anatomy is presented. In Section 2.4, the methods used to segment both the labyrinth and the intra-cochlear anatomy in the normal ear are detailed. Finally, in Section 2.5, the method to segment the intra-cochlear anatomy in the implanted ear using information obtained from the normal ear is presented.

2.1. Data

Table 1 summarizes the characteristics of the various sets of CT scans used for evaluation the method according to certain embodiments of the present invention. Age of subjects included in this study ranged from 18 to 90 years. The scans were acquired from several conventional scanners (GE BrightSpeed, LightSpeed Ultra; Siemens Sensation 16; and Philips Mx8000 IDT, iCT 128, and Brilliance 64) and a low-dose flat-panel volumetric CT (fpVCT) scanner (Xoran Technologies xCAT® ENT). Conventional CT scans of 10 subjects were used for symmetry analysis as described in Section 2.3. Conventional CT scans of 18 subjects were used for active shape model (ASM) creation as discussed in Section 2.4.2.1. fpVCT scans of 14 subjects were used for intensity gradient model (IGM) creation as discussed in Section 2.5.2. 18 CT-fpVCT pairs of scans were used for segmentation validation as discussed in section 2.5.3. Typical scan resolution for conventional CT scans is 768×768×145 voxels with 0.2×0.2×0.3 mm³ voxel size, and for fpVCT scans is 700×700×360 voxels and 0.3×0.3×0.3 or 0.4×0.4×0.4 mm³.

TABLE 1

Datasets Used

| Dataset | Purpose | Dataset size | Acquisition | | # of CIs | | |
|---|---|---|---|---|---|---|---|
| | | | Xoran fpVCT | Conventional | No CIs | One CI | Two CIs |
| 1 | Symmetry analysis | 10 | | X | X | | |
| 2 | ASM creation | 18 | | X | X | | |
| 3 | IGM creation | 14 | X | | X | | |
| 4 | Segmentation Validation | 6 | | X | X | | |
| | | | X | | | X | |
| | | 12 | | X | X | | |
| | | | X | | | | X |

Dataset 4 is used for segmentation validation. Each implanted ear in the dataset is automatically segmented in a post-implantation CT using the algorithms proposed in certain embodiments of this invention. For each of these ears, there is a pre-implantation CT that is used to generate gold standard segmentations to compare with the automatic segmentations for validation. Dataset 4 consists of two subgroups. The first (6 subjects) includes a set of conventional pre-implantation and low-dose post-implantation CTs of six unilateral CI recipients. The second (12 subjects) includes a set of conventional pre-implantation and low-dose post-implantation CTs of a group of 12 bilateral CI recipients. The second set is used to increase the size of the testing set without having to scan more unilateral CI recipients prior to demonstrating the efficacy of the technique of the present invention. To do so, the method register the pre- and post-implantation CTs and use the contralateral side of the pre-implantation CT rather than the contralateral side of the post-implantation CT in the algorithm. Using this technique, 30 datasets (6 in the first group and 12×2 in the second group) are available on which the unilateral segmentation algorithm can be tested. It should be noted that the second group of 24 ears from 12 subjects is not equivalent to ears from 24 subjects. While left and right ears generally have a different appearance in the post-implantation CT since the electrode array is positioned differently, differences in shape of anatomical structures between ears are not as large as inter-subject variations.

2.2. Image Registration Methods

Various processes in certain embodiments of the present invention rely on image-to-image registration. In this subsection, the affine and non-rigid registration methods are disclosed for image-to-image registration. Given a "fixed" image, i.e., an atlas, and a "floating" image, i.e. the image to be segmented, a multi-step process outlined in FIG. 6 is used for registration.

Figure 6:
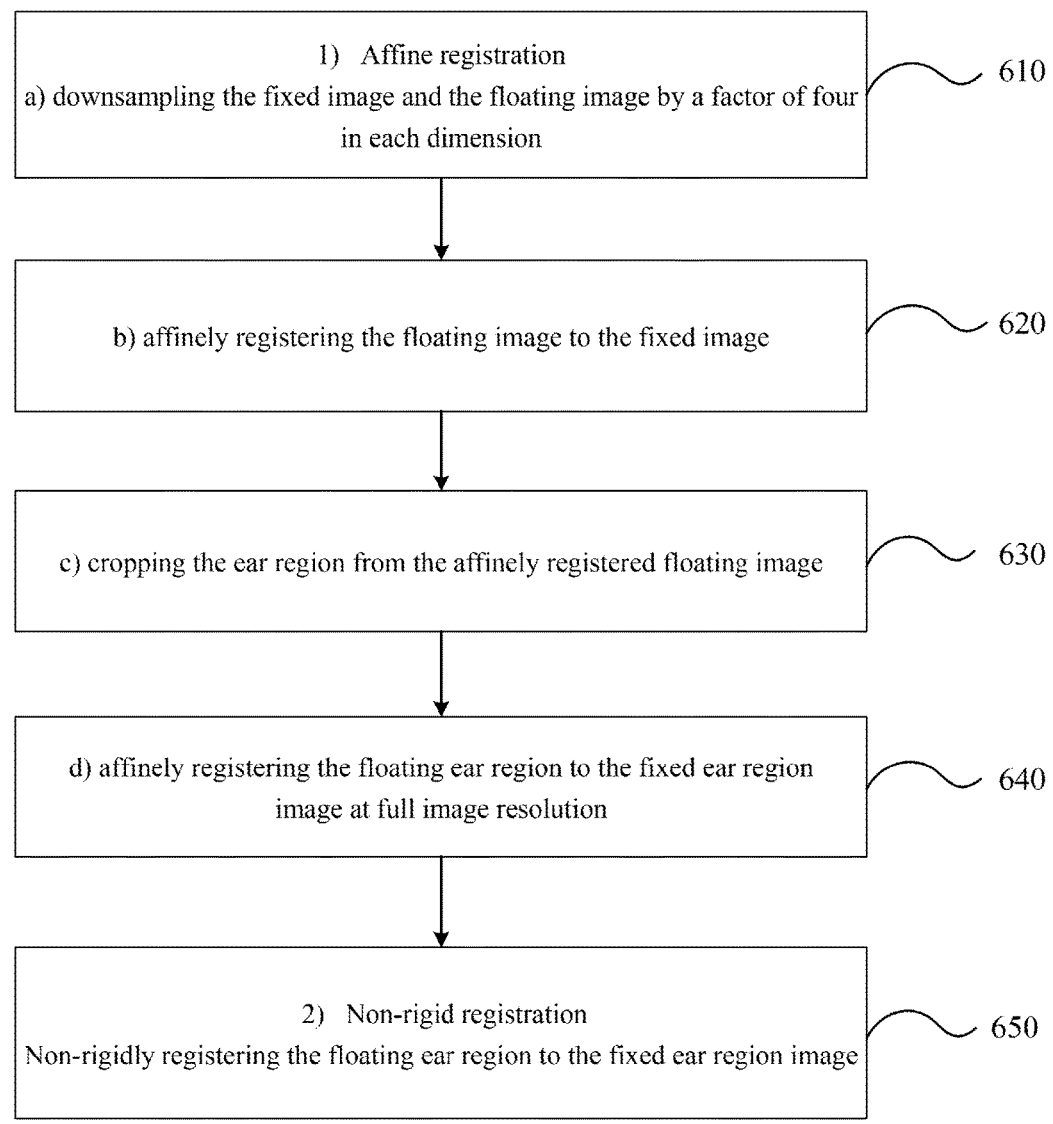
FIG. 6 shows a flowchart of an image registration process according to one embodiment of the present invention.

FIG. 6 shows a flowchart of an image registration process according to one embodiment of the present invention. In step 610, the fixed image and the floating image are downsampled, for example, by a factor in each dimension. In one embodiment, the factor can be 1-40. In one embodiment, the factor is about 2-10. In one embodiment, the factor is 4. In one embodiment, the factor in different dimensions can be the same or different. In step 620, the downsampled floating image is then affinely registered to the downsampled fixed image. In one embodiment, the affine registration is performed on the entire downsampled images. In other embodiments, the affine registration can also be performed on part of the downsampled images. Next, the registration is refined by limiting the region of interest to a pre-defined region that encompasses the ear structure. For example, in step 630, the ear region is cropped from the affinely registered floating image. Then, in step 640, the floating ear region is registered to the fixed ear region image at full image resolution. In certain embodiments, at this stage, the affine transformation is estimated at full resolution. In both the affinely registration of the downsampled images (step 620) and the region of interest of the images at full resolution (step 640), an intensity-based technique that uses Powell's direction set method and Brent's line search algorithm (Press et al., 1992) is adopted to optimize the mutual information (Wells III et al., 1996; Maes et al., 1997) between the images.

In step 650, the registration within the region of interest is further refined with a non-rigid registration step using the adaptive-bases algorithm (ABA) (Rhode et al., 2003). The ABA models the deformation field as a linear combination of a set of basis functions irregularly spaced over the image domain as shown in the following equation (1), $$v(x) = \sum_{i=1}^{N} c_i \Phi(x-x_i) \quad (1),$$

where x is a point in $\mathbb{R}^d$, with d being the dimensionality of images, the function $\Phi$ is Wu's compactly supported positive definite radial basis function (Wu, 1995), and $\{c_i\}_{i=1}^n \in \mathbb{R}^d$ is the set of basis function coefficients that are selected to optimize the normalized mutual information (Studholme et al., 1999) between the images. The optimization process uses a gradient descent algorithm to determine the direction of optimization, and a line minimization algorithm to calculate the optimal step in that direction. The final deformation field is computed using a multiresolution and multiscale approach. Multiresolution is achieved by creating a standard image pyramid, and multiscale is achieved by modifying the region of support and the number of basis functions. A large region of support models a transformation at a large scale. The algorithm is initialized on a low-resolution image with few basis functions. Then, the region of support of the basis functions is reduced as the algorithm progresses to finer resolutions and smaller scales (larger number of basis functions). Using this approach, the final deformation field is computed as $$v(x) = \sum_{k=1}^{M} v_k(x) \quad (2),$$

where M is the total number of combinations of scales and image resolutions used.

2.3. Symmetry Analysis

To establish that the ST, SV, SG, and the labyrinth are symmetric across ears, experiments on the set of pre-implantation CTs in dataset 1 (see Table 1) are conducted. Surfaces of the ST, SV, SG, and the labyrinth for both ears in each pre-implantation CT are identified using methods describe in Section 2.4. Then, the surfaces of one ear to the corresponding surfaces of the contralateral ear are registered using a standard point-based rigid-body registration method (Arun et al., 1987). Finally, distances between the points on each surface to the corresponding points on the registered surface are measured.

2.4. Segmentation of the Normal Ear

In one embodiment, an automatic ASM-based method (Noble et al., 2013; Noble et al., 2011a) is used to segment the ST, SV, and SG in the normal ear. The mean and maximum surface errors in segmenting the ST in fpVCTs are 0.18 and 0.9 mm. These values are 0.22 and 1.6 mm for the SV, and 0.15 and 1.3 mm for the SG, respectively.

The method developed for the automatic segmentation of the labyrinth relies on an active shape model. The following subsections describe how the labyrinth ASM model is created, how these models are used for segmentation purposes, and the study designed to test the accuracy of the results.

2.4.1. Labyrinth Active Shape Model Creation

An ASM of the labyrinth is created using the pre-implantation CTs in dataset 2 (see Table 1). One of these pre-implantation CTs is chosen to serve as a reference volume, and the remaining CTs are used as training volumes. The active shape model creation process is outlined in FIG. 7.

Figure 7:
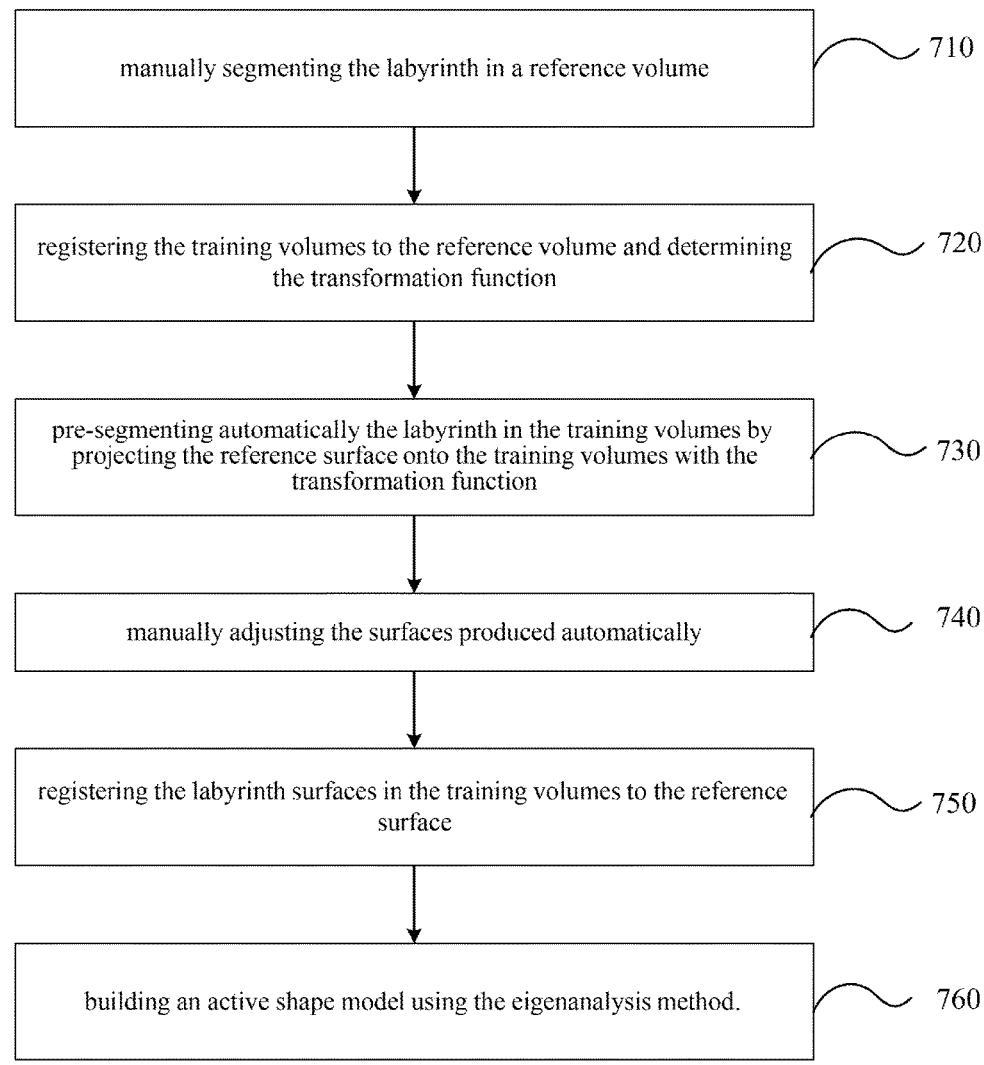
FIG. 7 shows a flowchart of a process for creating an active shape model (ASM) according to one embodiment of the present invention.

FIG. 7 shows a flowchart of a process for creating an active shape model (ASM) according to one embodiment of the present invention. As shown in FIG. 7, the process has six main steps.

In step 710, the labyrinth is segmented manually in the reference volume by an experienced otolaryngologist (TRM).

In step 720, the training volumes are registered to the reference volume using the multi-step registration techniques described in Section 2.2 (as shown in FIG. 6). The transformation function is determined according to the registration process.

In step 730, the labyrinth in each of the training volumes are pre-segmented by projecting the labyrinth surface from the reference volume onto each of the training volumes using the transformations computed in step 720.

In step 740, the surfaces produced in step 730 are manually edited to correct for possible segmentation errors caused by mis-registration. The steps 710-740 produce both segmented surfaces and a one-to-one point correspondence between points on the reference surface and points on each of the training surfaces. The procedures described in these four steps are similar to the approach described by Frangi et al. 2001.

In step 750, all the training surfaces are registered to the reference surface with a 7-Degree-Of-Freedom (DOF) transformation (three rotations, three translations, and one isotropic scale) computed with a standard least squares fitting method (Arun et al., 1987). Isotropic scaling is included as a DOF so that inter-subject differences in labyrinth scale are normalized.

Finally, in step 760, eigenanalysis is used to build the ASM, which is composed of the mean $\bar{x}$ and the eigenvectors $\{u_j\}$ of the covariance matrix X of the registered shapes, $$\{\lambda_j, u_j\}_{j=0}^{M-2} : \lambda_j u_j = X u_j \quad (3),$$

where M is the number of training shapes and $\{\lambda_j\}$ is the set of eigenvalues (Cootes et al., 1995).

2.4.2. Segmentation of the Labyrinth Using the Active Shape Model

Figure 8:
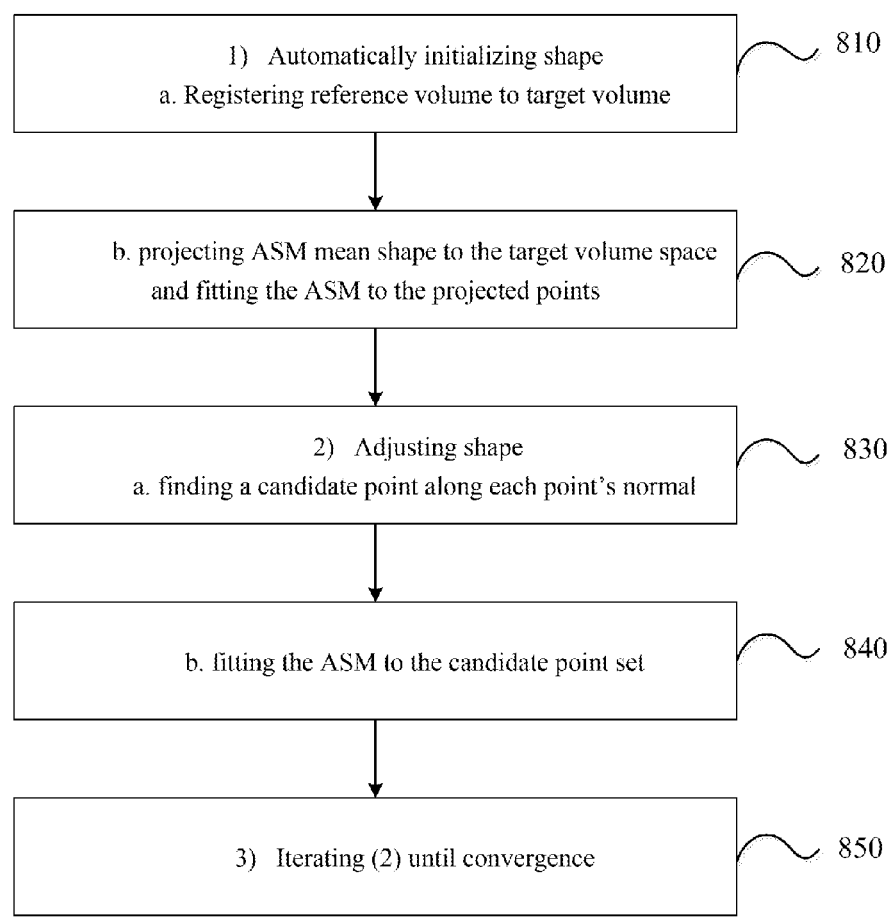
FIG. 8 shows a flowchart of a process of segmenting labyrinth in a target volume according to one embodiment of the present invention, based on the ASM built in FIG. 7.

Once an ASM of the labyrinth is built, the ASM is used to segment the labyrinth in a target volume using the segmentation process outlined in FIG. 8.

FIG. 8 shows a flowchart of a process of segmenting labyrinth in a target volume according to one embodiment of the present invention, based on the ASM built in FIG. 7.

In step 810, the ASM reference volume is registered to the target volume according to the procedure described in Section 2.2 (as shown in FIG. 6). Then in step 820, the ASM mean surface points are projected onto the target volume and the ASM is fit to these projected points. This produces initial segmentation, and the initial segmentation is then refined as follows. In step 830, for each point on the ASM surface $y = \{y_i\}_{i=0}^{N-1}$, a new candidate point $y'_i$ is found by searching for the point with the highest image intensity gradient within the interval [−1.35, 1.35] millimeter (mm) along the local surface normal $\hat{n}_i$, equivalently, $$y'_i = y_i + \Delta d \cdot k_{max} \cdot \hat{n}_i, \text{ where}$$

$$k_{max} = \arg\max_k(I(y_i + \Delta d \cdot (k+1) \cdot \hat{n}_i) - I(y_i + \Delta d \cdot (k-1) \cdot \hat{n}_i)), \quad (4),$$

for $k \in [-9, 9]$ and $\Delta d = 0.15$ mm, where $I(\cdot)$ is the image intensity at a given point. The approach of finding a point with the maximum gradient is similar to those investigated by Kass et al. (1988), Staib and Duncan (1992), Cohen and Cohen (1993), Cootes et al. (1995), Chakraborty et al. (1996), and Sakalli et al. (2006). Then, in step 840, the ASM is fit to the new candidate point set $y' = \{y'_i\}_{i=0}^{N-1}$ to obtain an adjusted shape $y'' = \{y''_i\}_{i=0}^{N-1}$. To perform the fitting procedure, first $y'$ is registered to the ASM mean shape $\bar{x}$ with a 7-DOF (three rotations, three translations, and one isotropic scale factor) transformation $\psi$. Then, the adjusted point set is computed using the equation:

$$y''_i = \psi^{-1}(\bar{x}_i + \Sigma_{j=0}^{K-1} b_j u_{j,i}), \quad (5)$$

with K being the number of eigenshapes used, where $$b_j = u_j^T(\omega(y') - \bar{x}) \quad (6)$$

The magnitude of $\{b_j\}_{j=0}^{K-1}$ is chosen such that the Mahalanobis distance from the adjusted shape to the mean shape is less than 3:

$$\sqrt{\sum_{j=0}^{K-1} \left(\frac{b_j^2}{\lambda_j}\right)} \leq 3$$

In step 850, the adjustment step is iterated until the constraint $1/N \Sigma_{i=0}^{N-1} \|y''_i - y_i\| < \epsilon$ is satisfied, where N is the number of points, and $\epsilon$ is empirically set to 0.01 mm.

2.4.3. Labyrinth Segmentation Validation

To validate the labyrinth segmentation method according to certain embodiments of the present invention, the reference volume is fixed and the method presented above is used to segment the remaining 17 training volumes in a leave-one-out approach. Distance between corresponding points on the automatic and manually generated surfaces is measured to quantitatively evaluate the agreement between the two. Specifically, for each point on the automatic surface, the Euclidean distance to the corresponding point on the manual surface is measured. Then, for each training volume, the mean and maximum of these distances are measured.

2.5. Segmentation of the Implanted Ear

Figure 9:
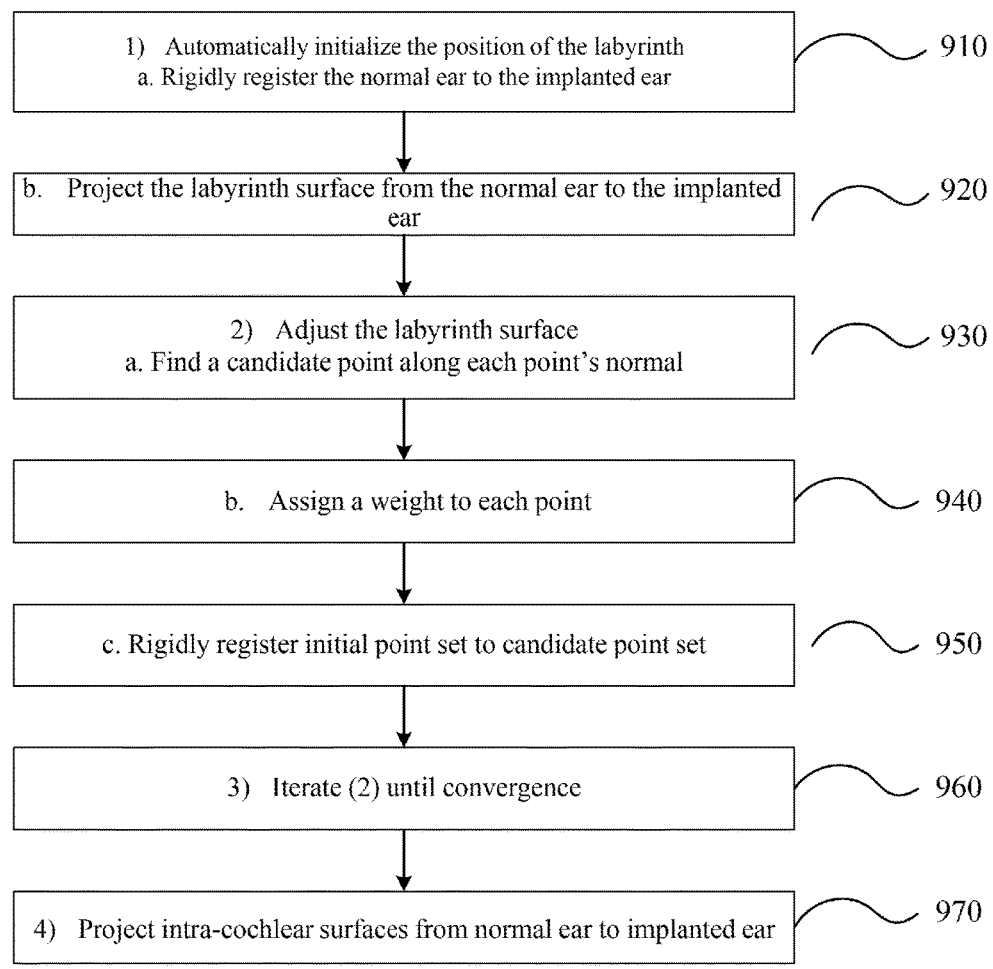
FIG. 9 shows a flowchart of a process of segmenting the intra-cochlear anatomy in an implanted ear according to one embodiment of the present invention.

The process to segment the intra-cochlear anatomy in an implanted ear is outlined in FIG. 9 according to certain embodiments of the present invention. FIG. 9 shows a flowchart of a process of segmenting the intra-cochlear anatomy in an implanted ear according to one embodiment of the present invention. In this process, the intra-cochlear anatomy in the implanted ear is not identified directly. Rather, the position of the labyrinth in the implanted ear is identified and is used as a landmark structure to determine the position of the intra-cochlear anatomy. First, an initial position of the labyrinth in the implanted ear is estimated using a procedure described in Section 2.5.1. Next, this estimation of the labyrinth position is iteratively refined using a procedure described in Section 2.5.2. Finally, the intra-cochlear anatomy in the implanted ear is determined by projecting the intra-cochlear surfaces segmented in the normal ear through the transformation that rigidly registers the labyrinth from the normal ear to the iteratively refined labyrinth in the implanted ear.

As shown in FIG. 9, in step 910, the normal ear is registered to the implanted ear. In step 920, the labyrinth surface from the normal ear is projected to the implanted ear. In step 930, a candidate point along each point's normal is found. In step 940, a weight is assigned to each point. In step 950, initial point set is rigidly registered to candidate point set. In step 960, the step 2) adjusting the labyrinth surface, including steps 930 and 940, are iterated until convergence. Finally in step 970, the intra-cochlear surfaces from normal ear are projected to the implanted ear. In certain embodiments of the present invention according to the above method, the information/location of the labyrinth surface in the implanted ear and the normal ear and the information/location of the surfaces of the SOIs in the normal ear are used to locate or evaluate the intra-cochlear (SOIs) surfaces of the implanted ear.

2.5.1. Segmentation Initialization Via Image-to-Image Registration

Figure 10:
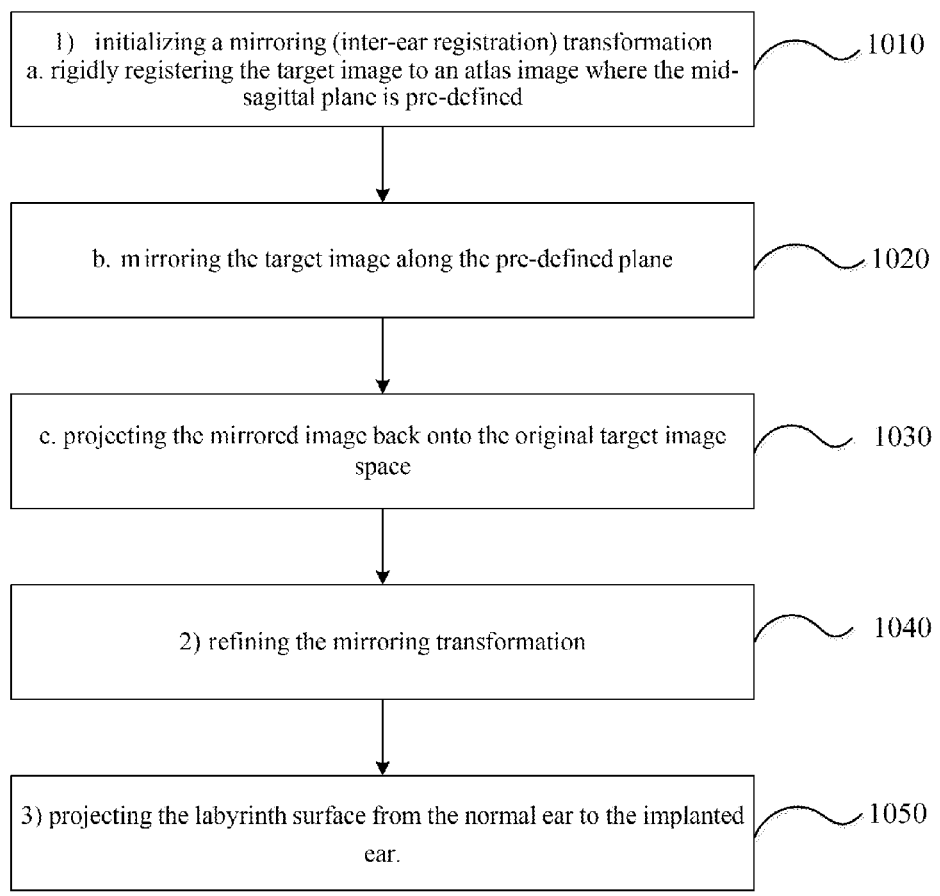
FIG. 10 shows a flowchart of the estimation of an initial position of the labyrinth in the implanted ear according to one embodiment of the present invention.

To estimate an initial position of the labyrinth in the implanted ear, the labyrinth surface from the normal contralateral ear is projected to the implanted ear. FIG. 10 shows a flowchart of the estimation of an initial position of the labyrinth in the implanted ear according to one embodiment of the present invention. The transformation used for projecting the labyrinth is the transformation that registers the normal ear to the implanted ear. Specifically, the steps listed in FIG. 10 are used to compute this transformation. In one embodiment, a mirroring transformation is estimated through registration to a volume (an atlas image) in which the mid-sagittal plane has been defined. Several approaches exist in the literature for accurate mid-sagittal extraction in magnetic resonance images (MRI) as well as other modalities (Ruppert et al. 2011, Prima et al. 2002, Liu et al. 2001, Tuzikov et al. 2003, and Smith et al. 1999). In one embodiment of the present invention, the approach selected by the inventors, while likely not as accurate as these dedicated methods, requires little extra processing because registration with a reference is already performed prior to segmentation and provides an estimation of the mirroring transformation that is accurate enough to initialize a subsequent refinement step. This is achieved by computing a rigid body transformation with an intensity-based method applied first to the entire but downsampled images then to a region of interest but at full resolution. This is similar to the process used in the first step of the process described in FIG. 6. As shown in FIG. 10, in step 1010, the target image is rigidly registered to an atlas image where the mid-sagittal plane is pre-defined. In step 1020, the target image along the pre-defined plane is mirrored. In step 1030, the mirrored image is projected back onto the original target image space. In step 1040, the mirroring transformation is refined. In step 1050, the labyrinth surface from the normal ear is projected to the implanted ear.

2.5.2. Segmentation Refinement Via Surface-to-Image Registration

To refine the position of the labyrinth, its position is iteratively adjusted. The refinement process is performed by iteratively finding candidate positions for each point $y_i$ on the labyrinth surface and rigidly registering the surface to those candidate points. This is similar to the iterative closest point surface registration algorithm introduced by Besl and McKay, 1992. At each iteration, the candidate position $y'_i$ is chosen for each point $y_i$ as:

$$y'_i = y_i + \Delta d \cdot k_{min} \cdot \widehat{n}_\iota \qquad (7)$$

where $\Delta d = 0.15$ mm, and $k_{min}$ is chosen to minimize the cost function:

$$k_{min} = \arg\min_k C_i(k) : k \in [-9, 9] \qquad (8)$$

The cost function $C_i(\cdot)$ designed for candidate selection at each ith point is a function of an intensity-gradient model (IGM) of the image at that point. A set of manual segmentations of the labyrinth in dataset 3 (see Table 1) is relied on to build the IGM. For each ith point on the jth training surface, $\{x_{ji}\}_{i=0}^{N-1}$, an intensity-gradient profile $g(x_{ji})$ along the local surface normal $\overline{n_{ji}}$ is extracted using the following equation (9):

$$g(x_{ji}) = [(I_j^{-10}(x_{ji}) - I_j^{-8}(x_{ji})), (I_j^{-9}(x_{ji}) - I_j^{-7}(x_{ji})), \ldots, (I_j^{8}(x_{ji}) - I_j^{10}(x_{ji}))]^T \qquad (9)$$

where $$I_j^k(x_{ji}) = I_j(x_{ji} + \Delta d \cdot k \cdot \widehat{n_{ji}}), \qquad (10)$$

$\Delta d = 0.015$ mm, and $I_j(\cdot)$ is the intensity of the jth training image at a given point. Finally, the IGM is defined as the set of $\{g(x_{ji})\}_{i=0}^{N-1}$ for $j \in [0, 1, \ldots, M-1]$, where N is the is the number of points composing each training surface, and M is the number of training surfaces.

The cost used for candidate point selection in equation 8 above is then designed as:

$$C_i(k) = \min_{j \in [0,1,\ldots,M-1]} \|g(y_i + \Delta d \cdot k \cdot \widehat{n}_\iota) - g(x_{ji})\| \qquad (11)$$

which defines the cost for selecting $y_i + \Delta d \cdot k \cdot \widehat{n}_\iota$ as a new candidate position for the ith point as the minimum Euclidean distance between the set of intensity-gradient profiles in the IGM and the intensity-gradient profile measured at that point. The standard approach is to compute the mean profile as well as the covariance of the profiles and determine candidate points by minimizing the Mahalanobis or Euclidean distance to the mean profile (Cootes et al. 1995, Cootes and Taylor 2001, Mitchell et al. 2001, Heimann et al. 2006, Heimann et al. 2007, Brejl and Sonka 2000, Tobon-Gomez et al. 2008). However, pilot experiments conducted by the inventors indicated that the approach according to certain embodiments of the present invention leads to superior final segmentation accuracy.

Finally, the rigid body transformation T is computed that registers the initial point set $\{y_i\}$ to the candidate point set $\{y'_i\}$ determined using equation/Eqn. (7) using a weighted least-squares approach (Sonka and Fitzpatrick, 2000), formulated as:

$$\arg_T \min \Sigma_{i=0}^{N-1} w_i^2 \|(T(y_i) - y'_i)\|^2 \qquad (12)$$

$\{w_i\}$ is a set of reliability weights that assigned to points using image intensity information derived from the images. Because the implant is very bright in the CT images, it obscures structure boundaries.

Figure 11:
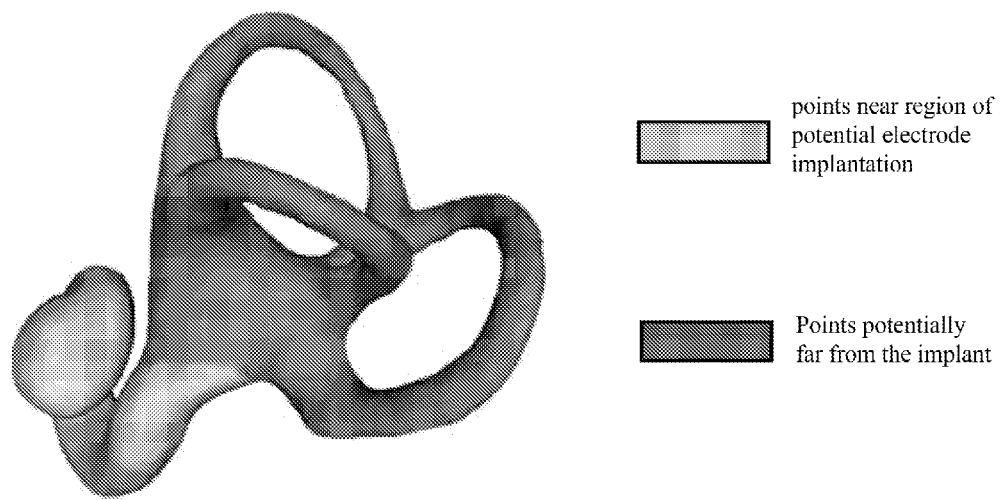
FIG. 11 shows a labyrinth surface image with points near region of potential electrode implantation colored blue and points potentially far from the implant colored yellow according to one embodiment of the present invention.

FIG. 11 shows a labyrinth surface image with points near region of potential electrode implantation colored blue and points potentially far from the implant colored yellow according to one embodiment of the present invention. Points in blue are used for computing R, the main parameter in the weight function. The remaining points of the labyrinth surfaces are shown in yellow. Points that are near high intensity regions are thus assigned low weight values and points away from bright regions are assigned high weight values. To compute the weight values, the intensity distribution of the image over a subset of labyrinth boundary points that are known a priori to lie far away from the electrode (region shown in blue in FIG. 11) are analyzed and this information is used to create a weight function that estimates the likelihood that each labyrinth surface point is located near an electrode. To do this, firstly, intensity profiles $r(z_i)$ at each ith point in the subset of surface points $\{z_i\}_{i=0}^{N'-1} \subset \{y_i\}_{i=0}^{N-1}$ that should lie far from the electrodes is extracted and is shown in blue in FIG. 11, using the equation:

$$r(z_i) = [I^{-10}(z_i), I^{-9}(z_i), \ldots, I^{10}(z_i)]^T \qquad (13)$$

where $$I^k(z_i) = I(z_i + \Delta d \cdot k \cdot \widehat{n}_\iota), \qquad (14)$$

$\Delta d = 0.15$ mm, and $I(\cdot)$ is the intensity of the target image at a given point. Then, at each iteration of the registration process, a weight for each point is computed as $$w_i = \begin{cases} 1.0 & \max(r(y_i)) < R \\ e^{\frac{(\max(r(y_i)) - R)^2}{2\sigma^2}} & \max(r(y_i)) \geq R \end{cases} \qquad (15)$$

where the value of R is experimentally determined (see details below) to be the 68th percentile of the distribution of the maximum values of $r(z_i)$ measured at $\{z_i\}_{i=0}^{N'-1}$, and $\sigma$ is the standard deviation of the same distribution, computed as:

$$\sigma = \left( \frac{1}{N'} \sum_{i=0}^{N'-1} (\max(r(z_i)) - \mu)^2 \right)^{1/2}.$$

As shown in FIG. 11, points in blue are the points used for computing R, the main parameter in the weight function. The remaining points of the labyrinth surfaces are shown in yellow.

The weight function in equation (15) is designed such that a weight value of 1.0 is assigned to points with a maximum value in their intensity profile less than R, and weight values that exponentially decay from 1.0 are assigned to points with a maximum value in their intensity profile greater than R. By assigning weights in this way, we achieve our goal, which is to constrain the registration to rely more on points located in regions that are less affected by the image artifacts produced by the implant.

Figure 12:
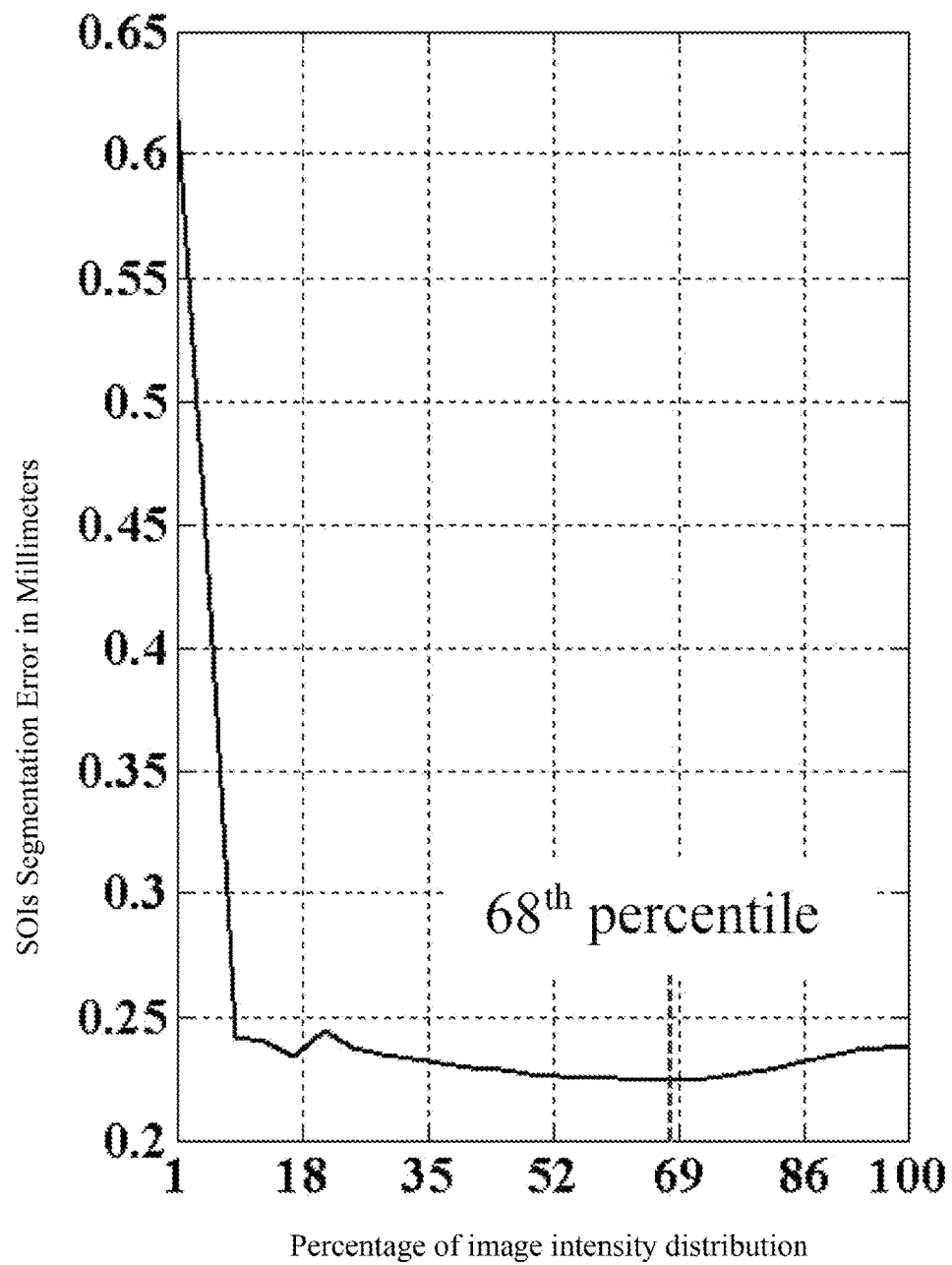
FIG. 12 shows mean error in the SOIs versus selection of R as a function of image intensity according to one embodiment of the present invention.

The value of R, as defined above, is customized for each target image because the intensity distribution in the images generated by the low-dose scanner used in this study vary across patients. The set of testing image pairs in dataset 4 is used to arrive at the value of R. First, R is sampled in increments of 4% percentiles in the distribution of maximum values of intensities $\{\max(r(z_i))\}_{i=0}^{N'}$, and the resulting SOI segmentation error on all testing image pairs are measured. Next, the value of R is selected as the value for which the overall mean segmentation error is the smallest. FIG. 12 shows mean error in the SOIs versus selection of R as a function of image intensity. Specifically, FIG. 12 shows a plot of the overall mean error for $R \in [\min(\{\max(r(z_i))\}_{i=0}^{N'}), \max(\{\max(r(z_i))\}_{i=0}^{N'})]$ in increments of 4 percentiles. As shown in FIG. 12, $R = 68^{th}$ percentile leads to the smallest segmentation error. This is the value, computed for each volume that is used to produce the results presented herein.

The surface-to-image registration step formulated in equation (12) is iterated until $1/N\Sigma_{i=0}^{N-1}\|T(y_i)-y_i\|<\epsilon$ is satisfied, where $\epsilon$ is empirically set to 0.01 mm. In summary, at each iteration, candidate points $\{y'_i\}$ are determined using equation (7), the weights $\{w_i\}$ are computed using equation (15), and the initial points $\{y_i\}$ are registered to the candidate points $\{y'_i\}$ using equation (12). Finally, the intra-cochlear anatomy in the implanted ear is segmented by projecting the intra-cochlear surfaces from the normal ear to the implanted ear through the iteratively refined inter-ear labyrinth registration transformation.

2.5.3. Validation

The method according to certain embodiments of the present invention is validated by automatically segmenting the post-implantation volumes in dataset 4 and measuring the resulting segmentation errors. The gold-standard surfaces that used for comparison were created in the pre-implantation volumes by manually editing surface points on segmentations that are automatically initialized by the pre-implantation CT segmentation techniques. Distances between corresponding points on the automatic and gold standard surfaces are measured to quantitatively evaluate the agreement between the two. Specifically, for each point on the automatic surface, the distance to the corresponding point on the gold standard surface is measured. Then, for each volume, the mean and maximum of the distances between all corresponding points are measured. To assess how much improvement our proposed surface-to-image registration refinement step provides, the method also measures segmentation errors achieved at initialization prior to performing the refinement step, which are the results that can be achieved using image registration alone. Finally the method according to certain embodiments of the present invention compares the technique to the best possible segmentation results that could be achieved using the contralateral ear registration method. These are obtained by registering directly the labyrinth surface in the normal ear to the gold standard labyrinth surface in the contralateral ear extracted from the pre-implantation CT with a 6-DOF (three rotations and three translations) point-based registration method that minimizes the RMS error between the two surfaces (Arun et al., 1987).

3. Results 3.1. Intra-Cochlear Anatomy and Labyrinth Symmetry

To demonstrate intra-subject inter-cochlear symmetry, the distance between the ST, SV, and SG surfaces rigidly registered across ears in dataset 1 are measured. These measurements are presented in Table 2.

Figure 13:
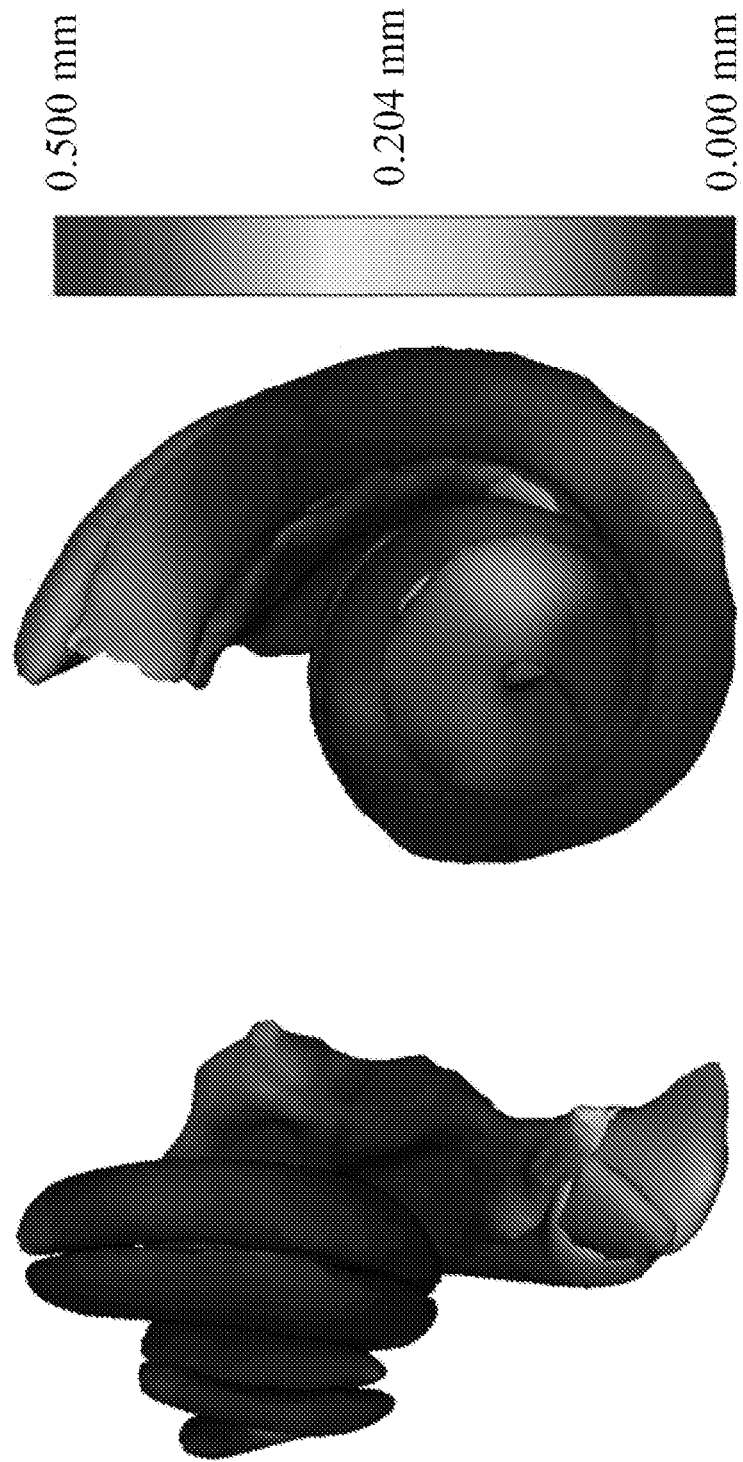
FIG. 13 shows subject one's ST, SV, and SG surfaces viewed in two different orientations according to one embodiment of the present invention.

FIG. 13 shows subject one's ST, SV, and SG surfaces viewed in two different orientations. The color at each point encodes the distance in mm to the corresponding point on the registered contralateral surfaces. That is, FIG. 13 shows the ST, SV, and SG surfaces from one ear colormapped with the distance to the registered contralateral surface for subject one. These distance values are smaller than the segmentation error for these structures as reported in (Noble et al., 2013) and (Noble et al., 2011a). Distance maxima are located in the same areas segmentation error maxima occur, i.e., at both the apical and basal ends of the cochlea. Segmentation errors occur at these locations due to the relative scarcity of local information available in the CT image to estimate the location of the intra-cochlear structures in these regions. This suggests that the small differences between the registered contralateral segmentations seen in FIG. 13 are most likely due to segmentation error, and that the intra-cochlear anatomy is indeed highly symmetric.

TABLE 2

Distances in millimeter between rigidly registered ST, SV and SG surfaces.

| Subjects | Scala Tympani (ST) | | Scala Vestibuli (SV) | | Spiral Ganglion (SG) | |
| --- | --- | --- | --- | --- | --- | --- |
| | Mean | Maximum | Mean | Maximum | Mean | Maximum |
| 1 | 0.099 | 0.287 | 0.088 | 0.243 | 0.092 | 0.350 |
| 2 | 0.051 | 0.159 | 0.054 | 0.108 | 0.064 | 0.159 |
| 3 | 0.019 | 0.071 | 0.018 | 0.054 | 0.030 | 0.113 |
| 4 | 0.049 | 0.121 | 0.044 | 0.133 | 0.046 | 0.118 |
| 5 | 0.059 | 0.160 | 0.059 | 0.161 | 0.063 | 0.245 |
| 6 | 0.063 | 0.144 | 0.055 | 0.155 | 0.073 | 0.212 |
| 7 | 0.087 | 0.328 | 0.064 | 0.164 | 0.065 | 0.162 |
| 8 | 0.049 | 0.115 | 0.045 | 0.119 | 0.067 | 0.193 |
| 9 | 0.055 | 0.139 | 0.050 | 0.142 | 0.049 | 0.160 |
| 10 | 0.058 | 0.176 | 0.058 | 0.140 | 0.068 | 0.172 |
| Overall | 0.059 | 0.328 | 0.054 | 0.243 | 0.062 | 0.350 |

Similar experiments are performed to demonstrate the existence of intra-subject symmetry in labyrinth anatomy. The distance between the labyrinth surfaces rigidly registered across ears in dataset 1 is measured. These measurements are presented in Table 3, and they are smaller than the labyrinth segmentation error reported in Section 3.2. These results suggest that the labyrinth is also highly symmetric.

TABLE 3

Distances in millimeter between rigidly registered labyrinth surfaces.

| Subject | 1 | 2 | 3 | 4 | 5 | 6 | 7 | 8 | 9 | 10 | Overall |
| --- | --- | --- | --- | --- | --- | --- | --- | --- | --- | --- | --- |
| Mean (mm) | 0.100 | 0.064 | 0.082 | 0.073 | 0.051 | 0.094 | 0.071 | 0.053 | 0.120 | 0.039 | 0.075 |
| Maximum (mm) | 0.239 | 0.226 | 0.276 | 0.264 | 0.171 | 0.348 | 0.329 | 0.185 | 0.320 | 0.140 | 0.348 |

3.2. Labyrinth Segmentation in the Normal Ear

The ASM of the labyrinth is built using 18 pre-implantation CTs (see dataset 2 in Table 1). A total of 9100 points compose each labyrinth shape. Table 4 presents the cumulative variations in percentage for the first nine principal components (eigenshapes). As shown in Table 4, the first nine principal components (eigenshapes) capture 90% of the shape variation in the training set. These eigenshapes were used in the ASM segmentation process. Previous studies suggest that the cochlea is fully formed at birth, and its size and shape does not change as an individual ages (Jeffery et al., 2004). Thus, it is of note that the models built are applicable for all age groups.

TABLE 4

Percent of labyrinth shape variations captured by the principal components of the shapes used for building the ASM of the labyrinth.

| Principal component | 1 | 2 | 3 | 4 | 5 | 6 | 7 | 8 | 9 |
|---|---|---|---|---|---|---|---|---|---|
| Cumulated Variations % | 25.07 | 42.98 | 55.02 | 66.64 | 74.31 | 78.95 | 83.21 | 87.08 | 90.00 |

Figure 14:
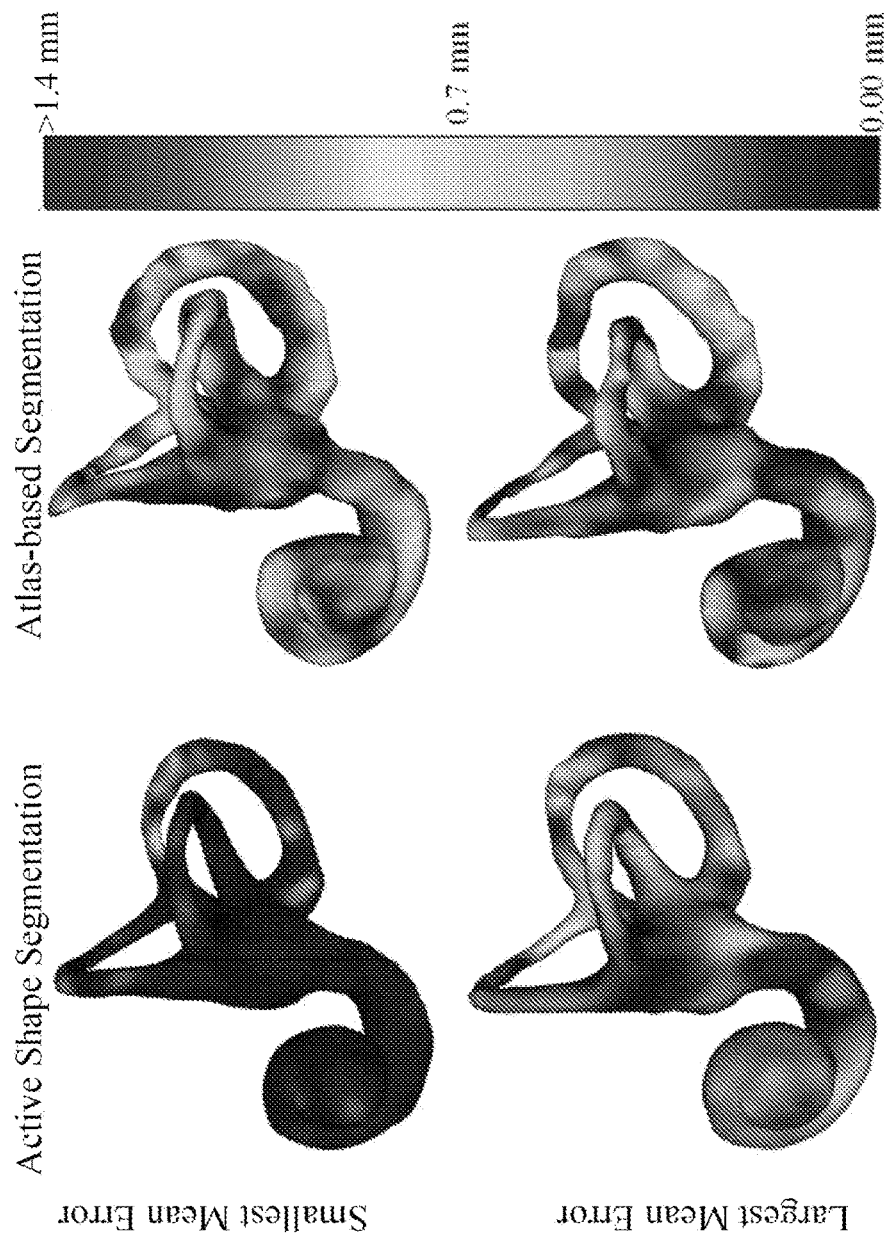
FIG. 14 shows renderings of the surfaces automatically segmented using both the ASM-based and atlas-based segmentation methods according to one embodiment of the present invention.

Table 5 presents the mean and maximum errors measured as the distance from each point on the automatically generated surface to the corresponding point on the manually generated surface. To illustrate the segmentation improvement provided by the ASM-based segmentation method, errors for surfaces generated using an atlas-based segmentation method are also shown. In this approach, the reference shape is simply projected onto the target volume using the transformation that registers the reference volume to the target volume. The overall mean and maximum errors for the ASM-based segmentation method are 0.239 and 1.623 mm, respectively. These are 0.452 and 2.407 mm for the atlas-based method. The mean and maximum errors for the ASM-based method are smaller than the atlas-based method for all subjects.

subject 16 (top row) and subject 2 (bottom row). The surfaces of the labyrinth in the left are generated by the ASM-based method, and the surfaces of the labyrinth in the right are generated by the atlas-based method. These surfaces are colormapped with the segmentation error. The top row in FIG. 14 shows the labyrinth of the subject with the smallest mean error (subject 16), and the bottom row shows the labyrinth with the largest mean error (subject 2). As can be seen, the surfaces generated using the atlas-based method have unnatural deformations, whereas the surfaces generated using the ASM-based method are smooth and resemble, as expected, the structure surfaces included in the ASM. As can also be seen in FIG. 14, the mean errors for the ASM-based method are sub-millimetric over most of the labyrinth surface.

3.3. Intra-Cochlear Anatomy Segmentation in the Implanted Ear

Figure 15B:
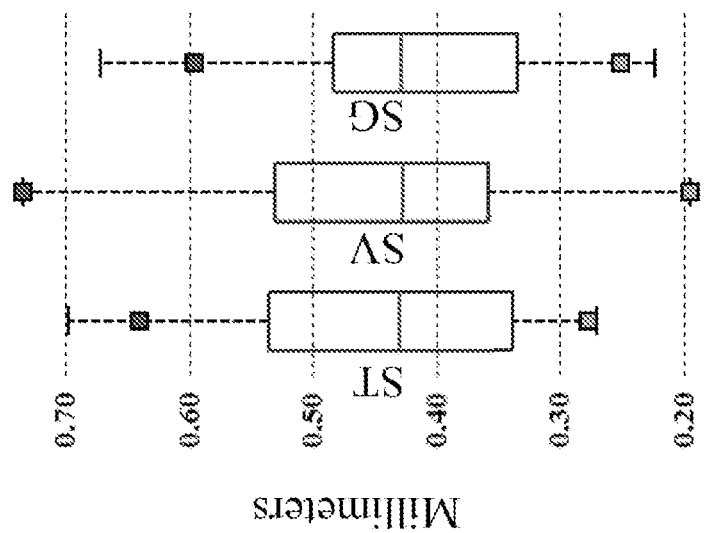
FIGS. 15A and 15B show quantitative results for the proposed segmentation method according to one embodiment of the present invention, where
Figure 15A:
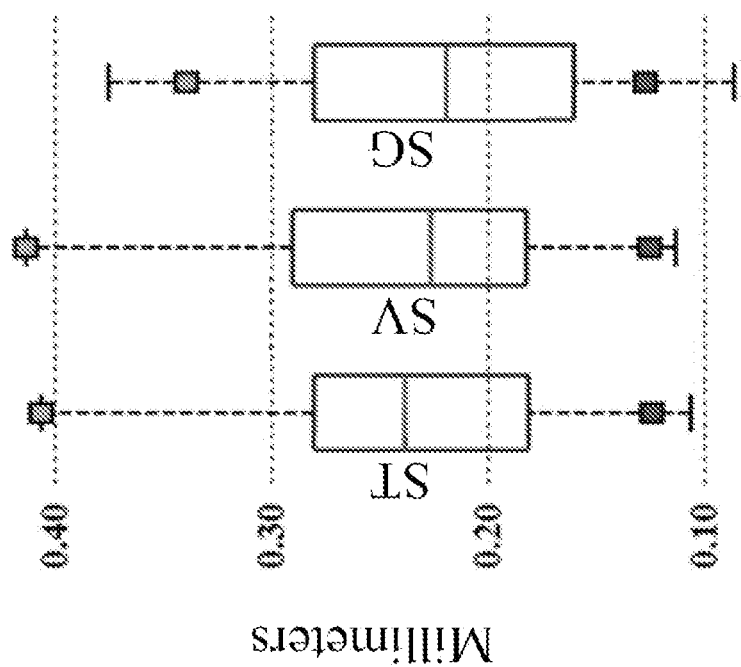

The gold-standard and automatically generated ST, SV, and SG surfaces for the 30 post-implantation ears in dataset 4 are compared quantitatively. FIGS. 15A and 15B show quantitative results for the proposed segmentation method. The green squares on the box plots are quantitative results for the subject with the smallest maximum error, and the red squares are quantitative results for the subject with the largest maximum error. Specifically, FIG. 15A shows box plots of the mean error for each SOI, and FIG. 15B shows the box plots of the maximum error for each SOI. In each box plot, the lower and upper bounds are the minimum and maximum values, respectively, the lower and upper whiskers are the first and third quartiles, respectively, and the red line is the second quartile or the median value. The overall mean and maximum errors for the proposed segmentation method are 0.224 and 0.734 mm, respectively. These results are comparable to those obtained by segmenting the SOIs in pre-implantation CT images using the methods described in (Noble et al., 2013; Noble et al., 2011a).

Figure 16:
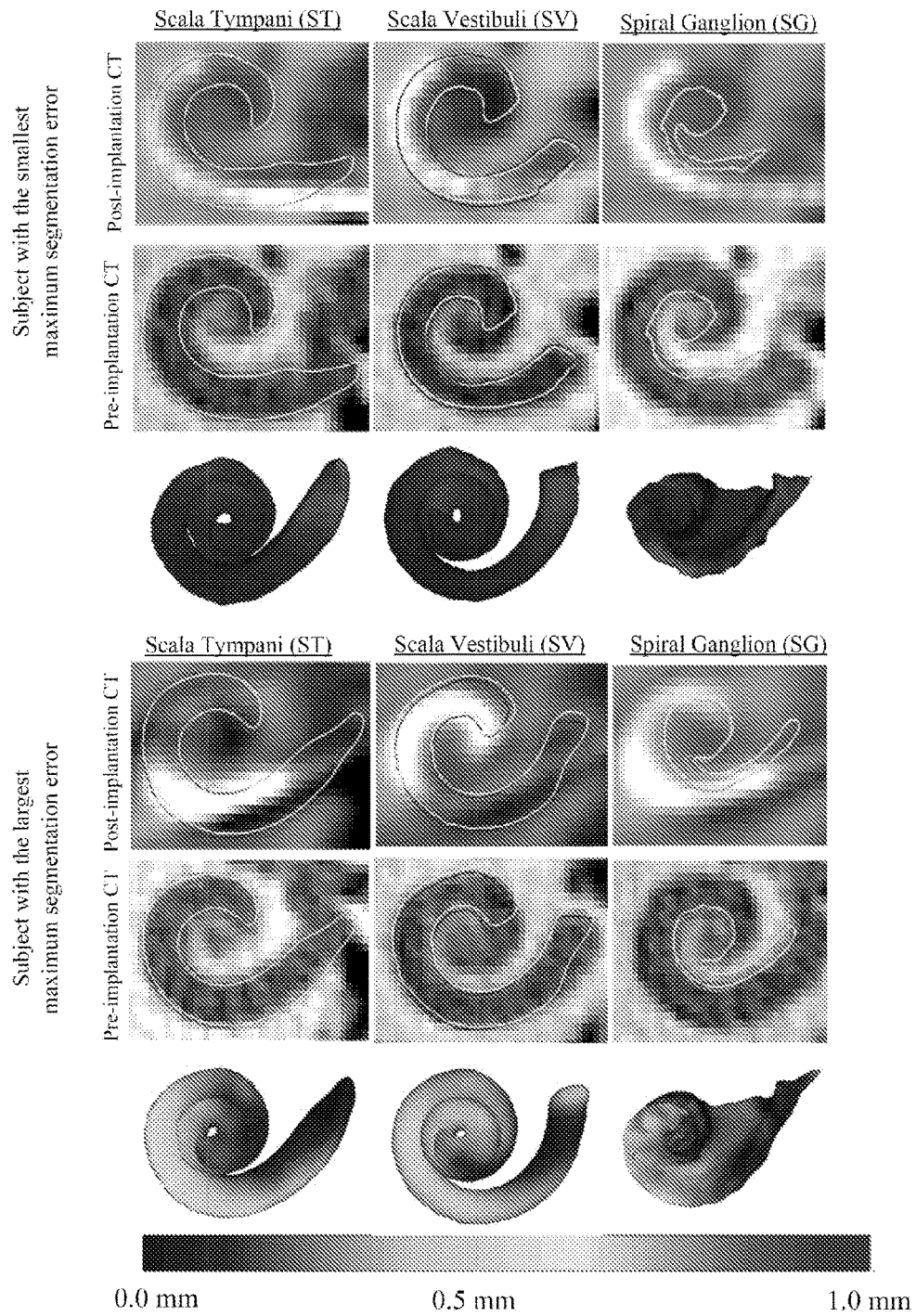
FIG. 16 shows qualitative segmentation results for the subject with the smallest maximum segmentation error and for the subject with the largest maximum segmentation error according to certain embodiment of the present invention.

FIG. 16 shows qualitative segmentation results for the subject with the smallest maximum segmentation error (green square box in FIGS. 15A and 15B) and for the subject with the largest maximum segmentation error (red square box in FIGS. 15A and 15B). Gold standard contours are

TABLE 5

Mean and maximum labyrinth segmentation errors in mm for both atlas-based and ASM-based methods.

Subjects

| | | 1 | 2 | 3 | 4 | 5 | 6 | 7 | 8 | 9 |
|---|---|---|---|---|---|---|---|---|---|---|
| Atlas-based Method | Mean | 0.442 | 0.408 | 0.395 | 0.370 | 0.458 | 0.414 | 0.534 | 0.616 | 0.489 |
| | Maximum | 2.153 | 2.156 | 1.757 | 1.450 | 2.140 | 2.009 | 2.407 | 2.299 | 1.536 |
| ASM-based Method | Mean | 0.254 | 0.335 | 0.236 | 0.280 | 0.240 | 0.256 | 0.174 | 0.232 | 0.238 |
| | Maximum | 0.963 | 1.623 | 1.017 | 0.679 | 1.123 | 1.223 | 0.664 | 1.398 | 0.993 |

| | | 10 | 11 | 12 | 13 | 14 | 15 | 16 | 17 | Overall |
|---|---|---|---|---|---|---|---|---|---|---|
| Atlas-based Method | Mean | 0.483 | 0.451 | 0.376 | 0.494 | 0.445 | 0.385 | 0.427 | 0.495 | 0.452 |
| | Maximum | 2.366 | 1.516 | 1.358 | 1.978 | 1.883 | 1.456 | 1.819 | 1.574 | 2.407 |
| ASM-based Method | Mean | 0.162 | 0.286 | 0.239 | 0.231 | 0.336 | 0.273 | 0.132 | 0.160 | 0.239 |
| | Maximum | 0.663 | 1.145 | 1.391 | 0.912 | 1.078 | 0.975 | 0.917 | 0.904 | 1.623 |

FIG. 14 shows renderings of the surfaces automatically segmented using both the ASM-based and atlas-based segmentation methods. Specifically, FIG. 14 shows automatically generated surfaces colormapped with errors in mm for shown in red, blue, and green for ST, SV, and SG, respectively, and automatically generated contours are in yellow. The contours shown are the ST (left panel), SV (middle panel), SG (right panel). Structure contours for gold-standard ST (red), gold-standard SV (blue), gold-standard SG (green), and automatic contours for all structures (yellow) are shown in a slice of a post-implantation image (top row) and a corresponding pre-implantation image (middle row). On the bottom panels the structure surfaces colormapped with segmentation errors are shown. The bottom part of FIG. 16 shows similar information for the subject with the largest maximum segmentation error (shown in red box on FIGS. 15A and 15B). For the subject with the smallest maximum error, there is excellent agreement between the gold-standard and automatic contours along the length of the structures. In the post-implantation CT, even though the structure boundary information is lost due to the presence of the implant, sub-millimetric segmentation accuracy is able to achieve for all SOIs. For the subject with the largest maximum error, some disagreement between the gold-standard and automatic contours can be seen along the length of the structures. However, as shown in the surface visualization, these errors are still sub-millimetric. FIG. 16 suggests that a number of voxels in the immediate proximity to the electrode array (bright voxels) do not lie within the segmentation-delineated borders of the scala tympani/scala vestibuli. This is caused by beam hardening and partial volume reconstruction artifacts that make the electrode appear larger in the images than it really is as shown in FIGS. 1, 2A, 2B, 3A and 3B.

Figures 17A, 17B:
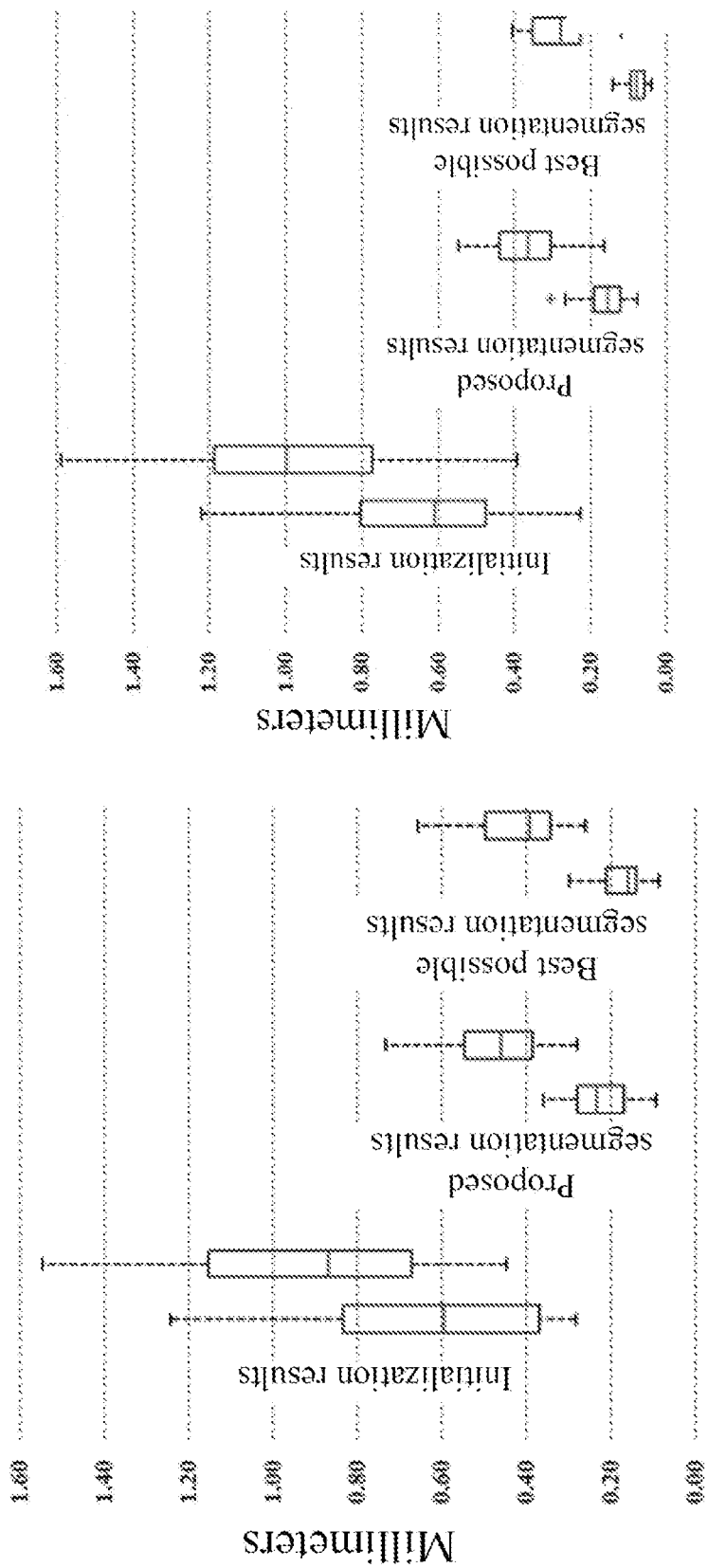
FIGS. 17A and 17B show various quantitative segmentation results for all 30 testing post-implantation CTs.

FIGS. 17A and 17B show various quantitative segmentation results for all 30 testing post-implantation CTs. FIG. 17A shows mean and maximum error box plots for the SOIs segmented using the initialization method (left), using the proposed segmentation method (middle). On the right are the mean and maximum error box plots for the best possible SOIs segmentation results. FIG. 17B shows the same information for the labyrinth. Left bar of FIG. 17A shows the mean and maximum error box plots for all SOIs (pooled ST, SV, and SG) segmented using only the inter-ear image registration-based initialization method described in Section 2.5.1. The overall mean and maximum errors are 0.639 and 1.545 mm, respectively. Middle bar of FIG. 17A shows the mean and maximum error box plots for all SOIs segmented using the proposed method. As shown in the plots, using the proposed segmentation method leads to a 64.94% and 52.49% reduction in mean and maximum segmentation errors, respectively. Right bar of FIG. 17A shows box plots of mean and maximum errors for the best segmentation results that could be achieved using the proposed method, as described in Section 2.5.3. The overall mean and maximum errors are 0.166 and 0.657 mm, respectively. This shows that the segmentation results we achieve in post-implantation CT are close to the best that are achievable, despite the lack of contrast in these images due to artifacts induced by the implanted electrode array. FIG. 17B shows the same information for the labyrinth.

4. Conclusion and Discussion

Image-guided CI programming strategies, like the ones in one aspect of the present invention, require accurate localization of the position of implanted electrodes relative to intra-cochlear anatomy. Until now, it has been possible to segment the SOIs, localize the electrodes, and compute the distance between the electrodes and intra-cochlear anatomy only for CI recipients for whom a pre-implantation CT has been acquired. In another aspect of the present invention, a method that does not require a pre-implantation CT is presented. This approach is to segment the labyrinth in the contralateral normal ear and use its position to segment the SOIs in the implanted ear by exploiting the intra-subject inter-ear symmetry. Symmetry analysis on ten subjects has been performed and the results suggest that both the SOIs and the labyrinth are highly symmetric.

To the best of the inventor's knowledge, there have been no methods proposed to automatically segment the labyrinth with a high degree of accuracy. The ASM-based method is validated in regard to 17 ears using a leave-one-out approach. The overall mean and maximum errors are 0.239 and 1.623 mm, respectively. As shown in the SOI segmentation validation study on 30 subjects, this level of accuracy is sufficient to segment the SOIs with sub-millimetric accuracy. In one aspect of the present invention which relied on a pre-implantation CT and achieved an average SOI segmentation error of 0.15 mm, excellent programming results have been obtained (Noble et al., 2013). In another aspect, using of the method that does not require a pre-implantation CT, the segmentation accuracy achieved is slightly larger (0.22 mm), but still small. It is anticipated that this slight reduction in segmentation accuracy will not negatively affect the improvement in hearing outcomes, as observed in the more than 60 patients that have participated in the ongoing study according to certain embodiments of the present invention (85% of these have reported substantial improvement in hearing). In subjects for whom a preoperative CT has not been acquired and a programming plan has been created using only a post-implantation CT, improvements in hearing can be confirmed.

The above discussed approach may not permit to identify intra-cochlear anatomy for bilateral implant users for whom a pre-implantation CT has not been acquired. However, in a further aspect, the segmentation techniques can be expanded (Reda et. al., 2014) to provide all cochlear implant subjects, including bilateral implant users, access to the image-guided programming method.

In certain embodiments of the present invention, the method as discussed above may be implemented by computer executable instructions, which may be stored in a non-transitory computer-readable medium.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the invention pertains without departing from its spirit and scope. Accordingly, the scope of the invention is defined by the appended claims rather than the foregoing description and the exemplary embodiments described therein.

5. References

Arun, K. S., Huang, T. S., and Blostein, S. D. "Least-squares fitting of two 3-D point sets," IEEE Trans. Pattern Anal. Mach. Intell., vol. 9, no. 5, pp. 698-700, September 1987.

Aschendorff, A., Kromeier, J., Klenzner, T., and Laszig, R., "Quality control after insertion of the nucleus contour and contour advance electrode in adults," Ear Hearing, vol. 28, pp. 75S-79S, April 2007.

Besl, P. J., McKay, H. D., "A method for registration of 3-D shapes," Pattern Analysis and Machine Intelligence, IEEE Transactions on, 14(2):239-256, 1992.

Brejl, M., Sonka, M., 2000. Object localization and border detection criteria design in edge-based image segmentation: automated learning from examples. IEEE Transactions on Medical Imaging 19 (10), 973-985.

Chakraborty, A., Staib, L., Duncan, J. S., Deformable boundary finding in medical images by integrating gradient and region information. IEEE Transactions on Medical Imaging 15 (6), 859-870, 1996.

Cohen, L., Cohen, I., Finite-element methods for active contours models and balloons for 2-D and 3-D images. IEEE Transactions on Pattern Analysis and Machine Intelligence 15 (11), 1131-1147, 1993.

Cootes, T. F., Taylor, C. J., Cooper, D. H., and Graham, J. "Active shape models—Their training and application," Comp. Vis. Image Understanding, vol. 61, no. 1, pp. 39-59, 1995.

Cootes, T. F., Taylor, C. J., Statistical models of appearance for medical image analysis and computer vision. In: Sonka, M., Hanson K. M. (Eds.), Proceedings of the SPIE Medical Imaging, vol. 4322, pp. 236-248, 2001.

Fitsum A. Reda, Jack H. Noble, Robert F. Labadie, and Benoit M. Dawant, "An artifact-robust technique for automatic segmentation of the labyrinth in post-cochlear implantation CT", Proc. SPIE 9034(9034-103), Medical Imaging 2014.

Heimann, T., Wolf, I., Meinzer, H.-P., Active shape models for a fully automated 3D segmentation of the liver—an evaluation on clinical data. In: Larsen, R., Nielsen, M., Sporring, J. (Eds), Proceeding of MICCAI, LNCS, vol. 4191. Springer, pp. 41-48, 2006.

Heimann, T., and Meinzer, H-P., "Statistical shape models for 3D medical image segmentation: A review", Medical Image Analysis, vol. 13(4), pp 543-563, August 2009.

Jack H. Noble, Theodore A. Schuman, Charles G. Wright, Robert F. Labadie, Benoit M. Dawant, "Automatic identification of cochlear implant electrode arrays for post-operative assessment", Proc. SPIE 7962(796217), Medical Imaging 201 lb.

Jeffery, N. and Spoor, F., Prenatal growth and development of the modern human labyrinth. Journal of Anatomy, 204: 71-92, 2004.

Kass, M., Witkin, A., Terzopoulos, D., Snakes: active contour models. International Journal of Computer Vision 1 (4), 321-331, 1988.

Liu, Y., Collins, R. T., and Rothfus, W. E., "Robust mid-sagittal plane extraction from normal and pathological 3D neuroradiology images," IEEE Trans. on Medical Imaging, vol. 20, no. 3, pp. 175-192, March 2001.

Maes, F., Collignon, A., Vandermeulen, D., Mrchal, G., and Suetens, P. "Multimodality image registration by maximization of mutual information," IEEE Trans. Med. Imag., vol. 16, no. 2, pp. 187-198, April 1997.

Mitchell, S. C., Lelieveldt, B. P. F., van der Geest, R. J., Bosch, H. G., Reiber, J. H. C., Sonka, M., Multistage hybrid active appearance model matching: segmentation of left and right ventricles in cardiac MR images. IEEE Transactions on Medical Imaging 20(5), 415-423, 2001.

Noble, J. H., Labadie, R. F., Majdani, O., Dawant, B. M., "Automatic Segmentation of Intracochlear Anatomy in Conventional CT," Biomedical Engineering, IEEE Transactions on, 58(9):2625-2632, September 2011a.

Noble, J. H., Gifford, R. H., Labadie, R. F., Dawant, B. M., "Statistical Shape Model Segmentation and Frequency Mapping of Cochlear Implant Stimulation Targets in CT," MICCAI 2012, 421-428, 2012.

Noble, J. H., Labadie, R. F., Gifford, R. H., Dawant, B. M., "Image-guidance enables new methods for customizing cochlear implant stimulation strategies," Neural Systems and Rehabilitation Engineering, IEEE Transactions on 21(5):820-829, September 2013.

Press, W. H., Flannery, B. P., Teukolsky, S. A., and Vetterling, W. T. Numerical Recipes in C, 2nd ed. (Cambridge University press, Cambridge, 1992), pp. 412-419.

Prima, S.; Ourselin, S.; Ayache N., "Computation of the mid-sagittal plane in 3-D brain images," Medical Imaging, IEEE Transactions on, vol. 21, no. 2, pp. 122, 148, February 2002.

Rohde, G. K, Aldroubi, A., and Dawant, B. M. "The adaptive bases algorithm for intensity-based nonrigid image registration," IEEE Trans. Med. Imaging, 22(11), 1470-1479 (2003).

Ruppert, G. C. S.; Teverovisky, L.; Chen-Ping Yu; Falaco, A. X.; Yanxi Liu, "A new symmetry based method for mid-sagittal plane extraction in neuroimages", Biomedical Imaging: From Nano to Macro, 2011 IEEE International Symposium on, On pages(s): 285-288.

Sakalli, M., Lam, K.-M., Yan, H., A faster converging snake algorithm to locate object boundaries. IEEE Transactions on Image Processing 15 (5), 1182-1191, 2006.

Schuman T. A., Noble J. H., Wright C. G., Wanna G. B., Dawant B. M., Labadie, R. F. "Anatomic Verification of a Novel, Non-rigid Registration Method for Precise Intrascalar Localization of Cochlear Implant Electrodes in Adult Human Temporal Bones Using Clinically-available Computerized Tomography," The Laryngoscope, 120 (11): 2277-2283, 2010.

Smith, S. M. and Jenkinson, M., "Accurate robust symmetry estimation," in Proc MICCAI '99, London, U K, 1999, pp. 308-317, Springer-Verlag.

Sonka, M. and Fitzpatrick, J. M. "Medical Image Processing and Analysis," Handbook of Medical Imaging, vol. 2, chapter 8:369-70, 2000.

Staib, L. H., Duncan, J. S., Boundary finding with parametically deformable models. IEEE Transactions on Pattern Analysis and Machine Intelligence 14 (11), 1061-1075, 1992.

Studholme, C., Hill, D. L. G., and Hawkes, D. J. "An overlap invariant entropy measure of 3D medical image alignment," Pattern Recognition, 32(1):71-86, 1999.

Tobon-Gomez, C., Butakoff, C., Aguade, S., Sukno, F., Moragas, G., Frangi, A. F., Automatic construction of 3D-ASM intensity models by simulating image acquisition: application to myocardial gated SPECT studies. IEEE Transactions on Medical Imaging 27 (11), 1655-1667, 2008.

Tuzikov, A. V., Colliot, O., Bloch, I., "Evaluation of the symmetry plane in 3D MR brain images," Pattern Recognition Letters, vol. 24, no. 14, pp. 2219-2233, October 2003.

U.S. Food and Drug Administration PMA, Cochlear implantation, No. 84002446, 21 Aug. 1995.

Wanna, G. B., Noble, J. H., McRackan, T. R., Dawant, B. M., Dietrich, M. S., Watkins, L. D., Rivas, A., Schuman, T. A., Labadie, R. F., "Assessment of electrode positions and audiological outcomes in bilateral cochlear implant patients," Otology & Neurotology, 32(3):428-432, 2011.

Wells III, W. M., Viola, P., Atsumi, H., Nakajima, S. and Kikinis, R. "Multi-modal volume registration by maximization of mutual information," Med. Image Anal., vol. 1, no. 1, pp. 35-51, March 1996.

Wilson B. S., Finley C. C., Lawson, D. T., Wolford, R. D., Eddington, D. K., Rabinowitz, W. M., "Better speech recognition with cochlear implants," Nature 352, 236-238, 1991.

Wilson B. S., Dorman M. F., "Cochlear implants: Current designs and future possibilities," J. Rehab. Res. Dev. 45(5): 695-730, 2008.

Wu, Z., "Multivariate compactly supported positive definite radial basis functions," Adv. Comput. Math., vol. 4, pp. 283-292, 1995.

What is claimed is:

1. A method for automatic segmentation of intra-cochlear anatomy of a patient having an implanted ear and a normal contralateral ear, comprising:
    obtaining at least one computed tomography (CT) image to generate a first image corresponding to the normal contralateral ear and a second image corresponding to the implanted ear;
    segmenting intra-cochlear surfaces of at least one first structure of interest (SOI) of the normal contralateral ear in the first image using at least one active shape model (ASM); and
    projecting the segmented intra-cochlear surfaces in the first image to the second image using a transformation function, thereby obtaining projected segmented intra-cochlear surfaces for the implanted ear in the second image.

2. The method of claim 1, wherein the transformation function is determined by rigidly registering a mirrored labyrinth surface of the first image to the second image.

3. The method of claim 1, wherein the step of segmenting intra-cochlear surfaces of the normal contralateral ear in the first image further comprises:
    segmenting a surface of a labyrinth of the normal contralateral ear in the first image using the at least one ASM.

4. The method of claim 3, wherein the labyrinth is a structure that externally bounds the intra-cochlear anatomy and includes three semi-circular canals.

5. The method of claim 1, wherein the at least one first SOI is scala tympani (ST), scala vestibuli (SV), or spiral ganglion (SG).

6. The method of claim 1, wherein the at least one ASM is a labyrinth ASM, a scala tympani (ST) ASM, a scala vestibuli (SV) ASM, a spiral ganglion (SG) ASM, or a combination thereof.

7. The method of claim 6, wherein the labyrinth ASM is created using a plurality of pre-implantation images, wherein one of the plurality of pre-implantation images is chosen as a reference volume and the remaining pre-implantation images are used as training volumes, and wherein the labyrinth ASM is created by:
    manually segmenting a reference labyrinth in the reference volume;
    registering training volumes to the reference volume and determining a registration transformation function for registering the training volumes to the reference volume;
    pre-segmenting automatically a training labyrinth in each of the training volumes by projecting a reference surface of the reference volume onto the training volumes with the registration transformation function to generate labyrinth surfaces in the training volumes;
    manually adjusting the generated labyrinth surfaces;
    registering the adjusted labyrinth surfaces to the reference surface; and
    building the labyrinth ASM using an eigenanalysis method.

8. The method of claim 7, wherein in the step of the registering the training volumes to the reference volume, the registration transformation function is determined by:
    downsampling a floating image and a fixed image, wherein the floating image is an image to be segmented, and the fixed image is an atlas image;
    affinely registering the floating image to the fixed image;
    cropping an ear region from the affinely registered floating image;
    affinely registering the ear region of the floating image to an ear region of the fixed image at full image resolution; and
    non-rigidly registering the ear region of the floating image to the ear region of the fixed image to obtain the registration transformation function.

9. The method of claim 8, wherein the floating image and the fixed image are downsampled by a factor of 1-40 in each dimension.

10. The method of claim 9, wherein the floating image and the fixed image are downsampled by a factor of 4 in each dimension.

11. The method of claim 7, wherein the step of segmenting intra-cochlear surfaces of the normal contralateral ear in the first image comprises:
    automatically initializing a shape in the first image, comprising:
        registering the reference volume of the ASM to a target volume, wherein the target volume is the first image; and
        projecting points of a mean shape of the ASM onto the target volume to generate a projected ASM surface and fitting the ASM to projected points on the projected ASM surface;
    adjusting the projected points, comprising:
        obtaining a candidate point set comprising a plurality of candidate points, wherein each candidate point is located along a normal direction of a corresponding projected point on the projected ASM surface; and
        fitting the projected ASM surface to the candidate point set; and
    iterating the step of adjusting the projected points until convergence.

12. The method of claim 11, wherein the step of registering the reference volume of the ASM to a target volume comprises:
    downsampling the first image and the ASM to generate a downsampled first image and a downsampled ASM;
    affinely registering the downsampled first image to the downsampled ASM;
    cropping an ear region from the affinely registered first image;
    affinely registering the ear region of the first image to an ear region of the ASM at full image resolution; and
    non-rigidly registering the ear region of the first image to the ear region of the ASM.

13. The method of claim 1, wherein the step of projecting the segmented intra-cochlear surfaces in the first image to the second image comprises:
    (1) automatically initializing a position of a projected labyrinth surface in the second image, comprising:
        rigidly registering a mirrored image of the first image to the second image; and
        projecting a surface of a labyrinth of the normal contralateral ear in the first image to the second image to obtain an initial point set of the projected labyrinth surface, wherein the initial point set comprises a plurality of initial points;

(2) adjusting the position of the projected labyrinth surface, comprising:

obtaining a candidate point set comprising a plurality of candidate points, wherein each candidate point is located along a normal direction of a corresponding initial point on the projected labyrinth surface;

assigning a weight to each candidate point of the candidate point set; and rigidly registering the initial point set to the candidate point set; and (3) iterating the step (2) until convergence.

14. The method of claim 13, wherein the step of projecting the surface of the labyrinth of the normal contralateral ear in the first image to the second image is performed using the transformation function, and the transformation function is determined by:

initializing a mirroring transformation, comprising:
rigidly registering a target image to an atlas image having a pre-defined mid-sagittal plane, wherein the target image is the second image and the atlas image is the first image;
mirroring the target image along the pre-defined mid-sagittal plane to form a mirrored image; and
projecting the mirrored image back onto the original target image;

refining the mirroring transformation; and
projecting the surface of the labyrinth of the normal contralateral ear in the first image to the second image.

15. A method for automatic segmentation of intra-cochlear anatomy of a patient having an implanted ear and a normal contralateral ear, comprising:

obtaining at least one computed tomography (CT) image to generate a first image corresponding to the normal contralateral ear and a second image corresponding to the implanted ear;

segmenting intra-cochlear surfaces of the normal contralateral ear in the first image; and projecting the segmented intra-cochlear surfaces in the first image to the second image using a transformation function, thereby obtaining projected segmented intra-cochlear surfaces for the implanted ear in the second image.

16. The method of claim 15, wherein the transformation function is determined by rigidly registering a mirrored labyrinth surface of the first image to the second image.

17. The method of claim 15, wherein the step of segmenting intra-cochlear surfaces of the normal contralateral ear in the first image comprises:

segmenting at least one first structure of interest (SOI) in the first image using at least one active shape model (ASM).

18. The method of claim 17, wherein the step of segmenting intra-cochlear surfaces of the normal contralateral ear in the first image further comprises:

segmenting a surface of a labyrinth of the normal contralateral ear in the first image using the at least one ASM.

19. The method of claim 18, wherein the labyrinth is a structure that externally bounds the intra-cochlear anatomy and includes three semi-circular canals.

20. The method of claim 17, wherein the at least one first SOI is scala tympani (ST), scala vestibuli (SV), or spiral ganglion (SG).

21. The method of claim 17, wherein the at least one ASM is a labyrinth ASM, a scala tympani (ST) ASM, a scala vestibuli (SV) ASM, a spiral ganglion (SG) ASM, or a combination thereof.

22. The method of claim 21, wherein the labyrinth ASM is created using a plurality of pre-implantation images, wherein one of the plurality of pre-implantation images is chosen as a reference volume and the remaining pre-implantation images are used as training volumes, and wherein the labyrinth ASM is created by:

manually segmenting a reference labyrinth in the reference volume;

registering training volumes to the reference volume and determining a registration transformation function for registering the training volumes to the reference volume;

pre-segmenting automatically a training labyrinth in each of the training volumes by projecting a reference surface of the reference volume onto the training volumes with the registration transformation function to generate labyrinth surfaces in the training volumes;

manually adjusting the generated labyrinth surfaces;
registering the adjusted labyrinth surfaces to the reference surface; and building the labyrinth ASM using an eigenanalysis method.

23. The method of claim 22, wherein in the step of the registering the training volumes to the reference volume, the registration transformation function is determined by:

downsampling a floating image and a fixed image, wherein the floating image is an image to be segmented, and the fixed image is an atlas image;

affinely registering the floating image to the fixed image;
cropping an ear region from the affinely registered floating image;

affinely registering the ear region of the floating image to an ear region of the fixed image at full image resolution; and non-rigidly registering the ear region of the floating image to the ear region of the fixed image to obtain the registration transformation function.

24. The method of claim 23, wherein the floating image and the fixed image are downsampled by a factor of 1-40 in each dimension.

25. The method of claim 24, wherein the floating image and the fixed image are downsampled by a factor of 4 in each dimension.

26. The method of claim 22, wherein the step of segmenting intra-cochlear surfaces of the normal contralateral ear in the first image comprises:

automatically initializing a shape in the first image, comprising:
registering the reference volume of the ASM to a target volume,
wherein the target volume is the first image; and
projecting points of a mean shape of the ASM onto the target volume to generate a projected ASM surface and fitting the ASM to projected points on the projected ASM surface;

adjusting the projected points, comprising:
obtaining a candidate point set comprising a plurality of candidate points, wherein each candidate point is located along a normal direction of a corresponding projected point on the projected ASM surface; and
fitting the projected ASM surface to the candidate point set; and iterating the step of adjusting the projected points until convergence.

27. The method of claim 26, wherein the step of registering the reference volume of the ASM to a target volume comprises:
downsampling the first image and the ASM to generate a downsampled first image and a downsampled ASM;
affinely registering the downsampled first image to the downsampled ASM;
cropping an ear region from the affinely registered first image;
affinely registering the ear region of the first image to an ear region of the ASM at full image resolution; and
non-rigidly registering the ear region of the first image to the ear region of the ASM.

28. The method of claim 15, wherein the step of projecting the segmented intra-cochlear surfaces in the first image to the second image comprises:
(1) automatically initializing a position of a projected labyrinth surface in the second image, comprising:
rigidly registering a mirrored image of the first image to the second image; and
projecting a surface of a labyrinth of the normal contralateral ear in the first image to the second image to obtain an initial point set of the projected labyrinth surface, wherein the initial point set comprises a plurality of initial points;
(2) adjusting the position of the projected labyrinth surface, comprising:
obtaining a candidate point set comprising a plurality of candidate points, wherein each candidate point is located along a normal direction of a corresponding initial point on the projected labyrinth surface;
assigning a weight to each candidate point of the candidate point set; and
rigidly registering the initial point set to the candidate point set; and
(3) iterating the step (2) until convergence.

29. The method of claim 28, wherein the step of projecting the surface of the labyrinth of the normal contralateral ear in the first image to the second image is performed using the transformation function, and the transformation function is determined by:
initializing a mirroring transformation, comprising:
rigidly registering a target image to an atlas image having a pre-defined mid-sagittal plane, wherein the target image is the second image and the atlas image is the first image;
mirroring the target image along the pre-defined mid-sagittal plane to form a mirrored image; and
projecting the mirrored image back onto the original target image;
refining the mirroring transformation; and
projecting the surface of the labyrinth of the normal contralateral ear in the first image to the second image.

30. A non-transitory computer-readable medium storing instructions which, when executed by a processor, cause a computer to perform a method for automatic segmentation of intra-cochlear anatomy of a patient having an implanted ear and a normal contralateral ear, the method comprising:
segmenting intra-cochlear surfaces of the normal contralateral ear in a first image corresponding to the normal contralateral ear; and
projecting the segmented intra-cochlear surfaces in the first image to a second image corresponding to the implanted ear using a transformation function, thereby obtaining projected segmented intra-cochlear surfaces for the implanted ear in the second image,
wherein the first image and the second image are generated from at least one computed tomography (CT) image.

31. The non-transitory computer-readable medium of claim 30, wherein the transformation function is determined by rigidly registering a mirrored labyrinth surface of the first image to the second image.

32. The non-transitory computer-readable medium of claim 30, wherein the step of segmenting intra-cochlear surfaces of the normal contralateral ear in the first image comprises:
segmenting at least one first structure of interest (SOI) in the first image using at least one active shape model (ASM).

33. The non-transitory computer-readable medium of claim 32, wherein the step of segmenting intra-cochlear surfaces of the normal contralateral ear in the first image further comprises:
segmenting a surface of a labyrinth of the normal contralateral ear in the first image using the at least one ASM.

34. The non-transitory computer-readable medium of claim 33, wherein the labyrinth is a structure that externally bounds the intra-cochlear anatomy and includes three semicircular canals.

35. The non-transitory computer-readable medium of claim 32, wherein the at least one first SOI is scala tympani (ST), scala vestibuli (SV), or spiral ganglion (SG).

36. The non-transitory computer-readable medium of claim 32, wherein the at least one ASM is a labyrinth ASM, a scala tympani (ST) ASM, a scala vestibuli (SV) ASM, a spiral ganglion (SG) ASM, or a combination thereof.

37. The non-transitory computer-readable medium of claim 36, wherein the labyrinth ASM is created using a plurality of pre-implantation images, wherein one of the plurality of pre-implantation images is chosen as a reference volume and the remaining pre-implantation images are used as training volumes, and wherein the labyrinth ASM is created by:
manually segmenting a reference labyrinth in the reference volume;
registering training volumes to the reference volume and determining a registration transformation function for registering the training volumes to the reference volume;
pre-segmenting automatically a training labyrinth in each of the training volumes by projecting a reference surface of the reference volume onto the training volumes with the registration transformation function to generate labyrinth surfaces in the training volumes;
manually adjusting the generated labyrinth surfaces;
registering the adjusted labyrinth surfaces to the reference surface; and
building the labyrinth ASM using an eigenanalysis method.

38. The non-transitory computer-readable medium of claim 37, wherein in the step of the registering the training volumes to the reference volume, the registration transformation function is determined by:
downsampling a floating image and a fixed image, wherein the floating image is an image to be segmented, and the fixed image is an atlas image;
affinely registering the floating image to the fixed image;
cropping an ear region from the affinely registered floating image;

affinely registering the ear region of the floating image to an ear region of the fixed image at full image resolution; and non-rigidly registering the ear region of the floating image to the ear region of the fixed image to obtain the registration transformation function.

39. The non-transitory computer-readable medium of claim 38, wherein the floating image and the fixed image are downsampled by a factor of 1-40 in each dimension.

40. The non-transitory computer-readable medium of claim 39, wherein the floating image and the fixed image are downsampled by a factor of 4 in each dimension.

41. The non-transitory computer-readable medium of claim 37, wherein the step of segmenting intra-cochlear surfaces of the normal contralateral ear in the first image comprises:

automatically initializing a shape in the first image, comprising:
registering the reference volume of the ASM to a target volume, wherein the target volume is the first image; and
projecting points of a mean shape of the ASM onto the target volume to generate a projected ASM surface and fitting the ASM to projected points on the projected ASM surface;

adjusting the projected points, comprising:
obtaining a candidate point set comprising a plurality of candidate points, wherein each candidate point is located along a normal direction of a corresponding projected point on the projected ASM surface; and
fitting the projected ASM surface to the candidate point set; and iterating the step of adjusting the projected points until convergence.

42. The non-transitory computer-readable medium of claim 41, wherein the step of registering the reference volume of the ASM to a target volume comprises:

downsampling the first image and the ASM to generate a downsampled first image and a downsampled ASM;
affinely registering the downsampled first image to the downsampled ASM;
cropping an ear region from the affinely registered first image;
affinely registering the ear region of the first image to an ear region of the ASM at full image resolution; and non-rigidly registering the ear region of the first image to the ear region of the ASM.

43. The non-transitory computer-readable medium of claim 30, wherein the step of projecting the segmented intra-cochlear surfaces in the first image to the second image comprises:

(1) automatically initializing a position of a projected labyrinth surface in the second image, comprising:
rigidly registering a mirrored image of the first image to the second image; and
projecting a surface of a labyrinth of the normal contralateral ear in the first image to the second image to obtain an initial point set of the projected labyrinth surface, wherein the initial point set comprises a plurality of initial points;

(2) adjusting the position of the projected labyrinth surface, comprising:
obtaining a candidate point set comprising a plurality of candidate points, wherein each candidate point is located along a normal direction of a corresponding initial point on the projected labyrinth surface;
assigning a weight to each candidate point of the candidate point set; and
rigidly registering the initial point set to the candidate point set; and (3) iterating the step (2) until convergence.

44. The non-transitory computer-readable medium of claim 43, wherein the step of projecting the surface of the labyrinth of the normal contralateral ear in the first image to the second image is performed using the transformation function, and the transformation function is determined by:

initializing a mirroring transformation, comprising:
rigidly registering a target image to an atlas image having a pre-defined mid-sagittal plane, wherein the target image is the second image and the atlas image is the first image;
mirroring the target image along the pre-defined mid-sagittal plane to form a mirrored image; and
projecting the mirrored image back onto the original target image;

refining the mirroring transformation; and
projecting the surface of the labyrinth of the normal contralateral ear in the first image to the second image.

* * * * *

UNITED STATES PATENT AND TRADEMARK OFFICE
CERTIFICATE OF CORRECTION

PATENT NO. : 9,589,361 B2
APPLICATION NO. : 14/766402
DATED : March 7, 2017
INVENTOR(S) : Fitsum A. Reda et al.

Page 1 of 1

It is certified that error appears in the above-identified patent and that said Letters Patent is hereby corrected as shown below:

In the Specification

Column 1, Lines 29-33: reading "This invention was made with government support under grant numbers R01DC008408, R21DC012620 and R01DC010184 awarded by the National Institute on Deafness and Other Communication Disorders. The government has certain rights in the invention."

Should read as follows:
-- This invention was made with government support under grant numbers DC008408, DC012620, and DC010184 awarded by the National Institutes of Health. The government has certain rights in the invention. --

Signed and Sealed this
Third Day of December, 2019

Andrei Iancu
*Director of the United States Patent and Trademark Office*